United States Patent
Monteiro et al.

(10) Patent No.: US 10,428,020 B2
(45) Date of Patent: Oct. 1, 2019

(54) ANTIMICROBIAL COMPOUNDS AND NANOSTRUCTURES

(71) Applicant: THE BOEING COMPANY, Chicago, IL (US)

(72) Inventors: Michael Monteiro, Brisbane (AU); Jason W. Armstrong, Brisbane (AU)

(73) Assignee: THE BOEING COMPANY, Chicago, IL (US)

( * ) Notice: Subject to any disclaimer, the term of this patent is extended or adjusted under 35 U.S.C. 154(b) by 0 days.

(21) Appl. No.: 15/838,751

(22) Filed: Dec. 12, 2017

(65) Prior Publication Data

US 2018/0362462 A1    Dec. 20, 2018

Related U.S. Application Data

(60) Provisional application No. 62/521,040, filed on Jun. 16, 2017.

(51) Int. Cl.
| | | |
|---|---|---|
| C07D 207/416 | (2006.01) | |
| A61K 31/4188 | (2006.01) | |
| A61K 31/4402 | (2006.01) | |
| A61K 31/4015 | (2006.01) | |

(52) U.S. Cl.
CPC ...... *C07D 207/416* (2013.01); *A61K 31/4015* (2013.01); *A61K 31/4188* (2013.01); *A61K 31/4402* (2013.01)

(58) Field of Classification Search
CPC ............ A61K 31/4015; A61K 31/4188; A61K 31/4402; C07D 207/416
See application file for complete search history.

(56) References Cited

PUBLICATIONS

Jin Geng, et al., Site-Directed Conjugation of "Clicked" Glycopolymers to Form Glycoprotein Mimics: Binding to Mammalian Lectin and Induction of Immunological Function, J. Am. Chem. Soc. 2007, 129, 15156-15163.
Carl N. Urbani, et al., Nanoreactors for Aqueous RAFT-Mediated Polymerizations, Macromolecules 2009, 42, 3884-3886.
Tzu-Yu Liu, et al., Self-Adjuvanting Polymer Peptide Conjugates as Therapeutic Vaccine Candidates against Cervical Cancer, Biomacromolecules 2013, 14, 2798-2806.
Zhongfan Jia, et al., Multifunctional Nanoworms and Nanorods through a One-Step Aqueous Dispersion Polymerization, J. Am. Chem. Soc. 2014, 136, 5824-5827.
Holdsworth, Ci et al., RAFT-Mediated Emulsion polymerization of Styrene with a Thermoresponsive MacroCTA Polymer, pp. 1-27; 2016; p. 5, paragraph 3; p. 6, paragraphs 1-3.
Vogt, AP, Macromolecular Design Via Combinations of Controlled Radical Polymerization Techniques and Click Chemistry, Doctoral Thesis, Southern Methodist University, pp. 1-73, 2009; p. 72, Scheme 3.2.
Koumba, AMB, Design, Synthesis and Characterisation of Amphiphilic Symmetrical Triblock Copolymers by the RAFT Process: Their Self-Organisation in Dilute and Concentrated Aqueous Solutions, Doctoral Thesis, Universitat Potsdam, pp. 1-79, 2009; p. 79, see structure Figure 4.4.
Zhang, W et al., One-Pot Synthesis of Poly(methacrylic acid-co-poly(ethylene oxide) methyl ether methacrylate)-b-polystyrene Amphiphilic Block Copolymers and Their Self-Assemblies in Water via RAFT-Mediated Radical Emulsion Polymerization. A Kinetic Study, Macromolecules, 44(19), pp. 7584-7593, 2011; abstract only.

(Continued)

*Primary Examiner* — Valerie Rodriguez-Garcia
(74) *Attorney, Agent, or Firm* — Patterson + Sheridan, LLP

(57) ABSTRACT

The present disclosure provides compounds and nanostructures having one or more quaternary ammonium salts, compositions including the compounds and nanostructures, and methods useful for treating conditions using the compounds, nanostructures, and compositions. In at least one aspect, a compound is represented by formula (I):

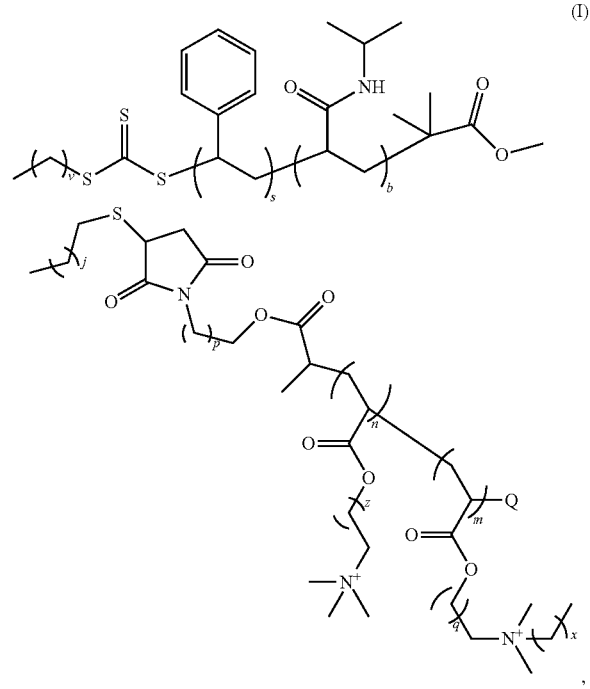

or a pharmaceutically acceptable salt thereof, wherein:
Q is fluoro, chloro, bromo, or iodo;
each of s, b, and n is independently an integer from about 10 to about 100; and
each of v, j, p, z, q, x and m is independently an integer from 1 to about 20.

22 Claims, 8 Drawing Sheets

(56) References Cited

PUBLICATIONS

Ma, J et al., Preparation of Thermo-Responsive and Cross-Linked Fluorinated Nanoparticles via RAFT-Mediated Aqueous Polymerization in Nanoreactors, Molecules 22(152), pp. 1-13, Jan. 25, 2017; pago 3, see structure, Figure 1C.

PCT Notification of Transmittal of the International Search Report and the Written Opinion of the International Searching Authority, or the Declaration for Application No. PCT/US18/37360 dated Aug. 28, 2018.

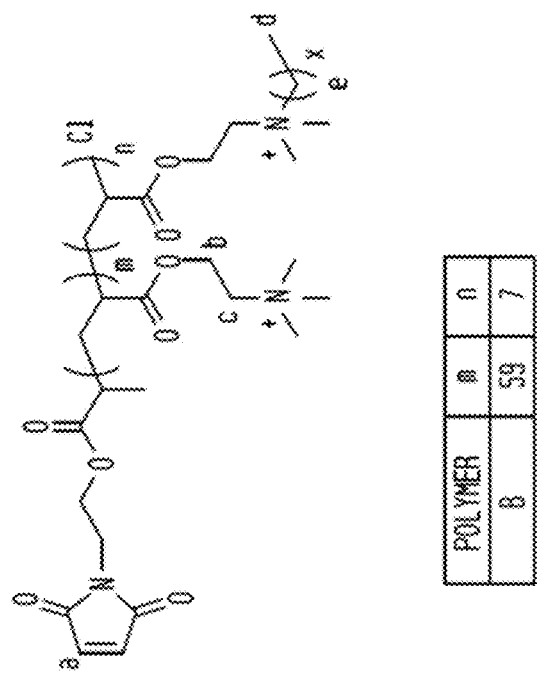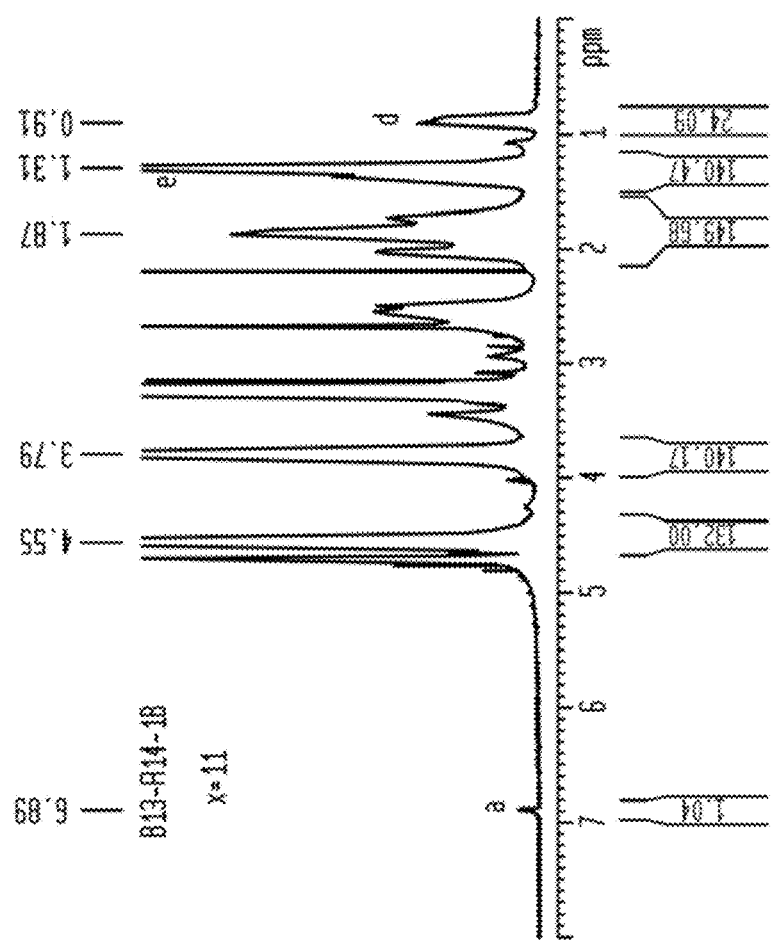
FIG. 2B

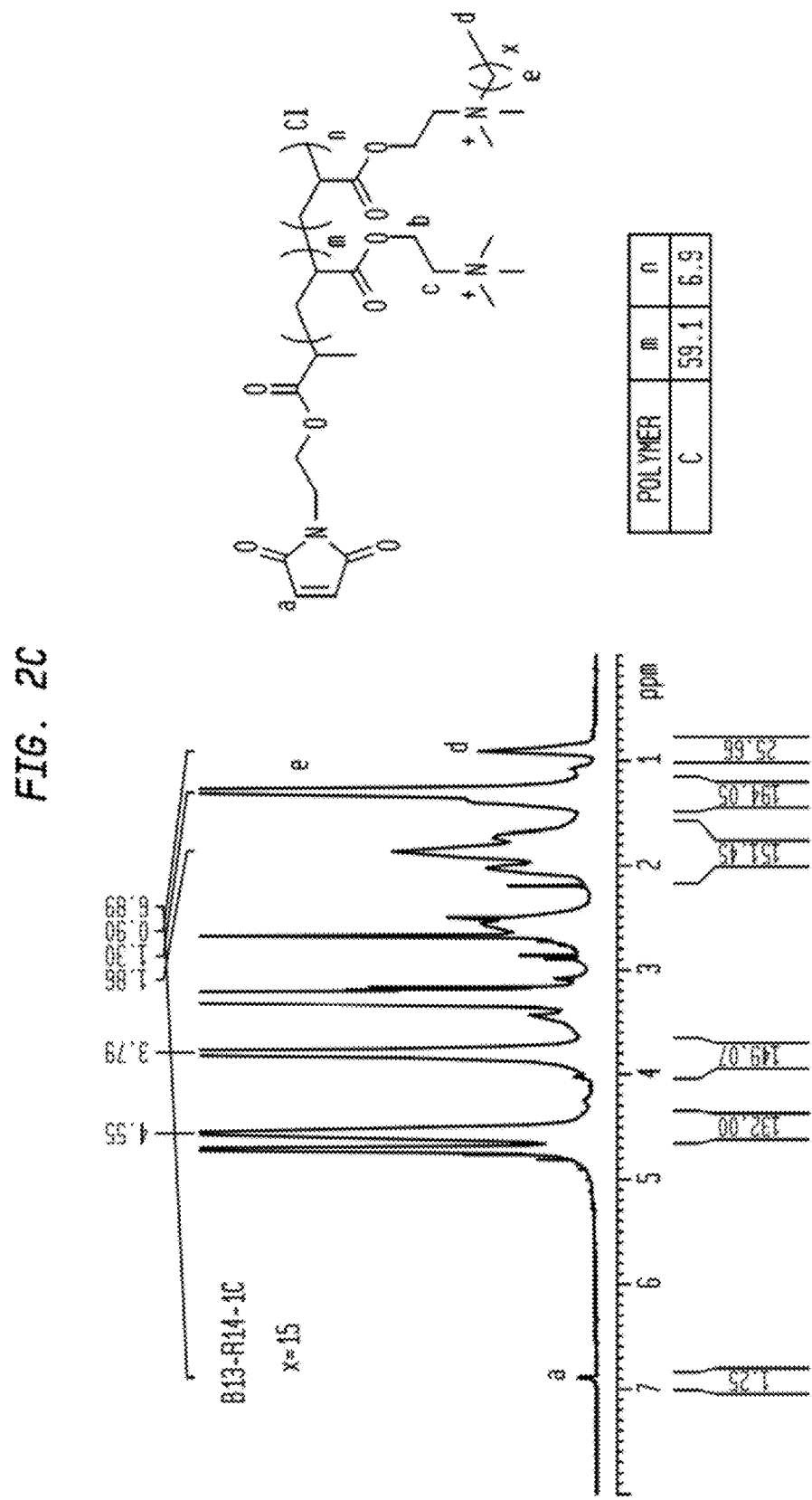

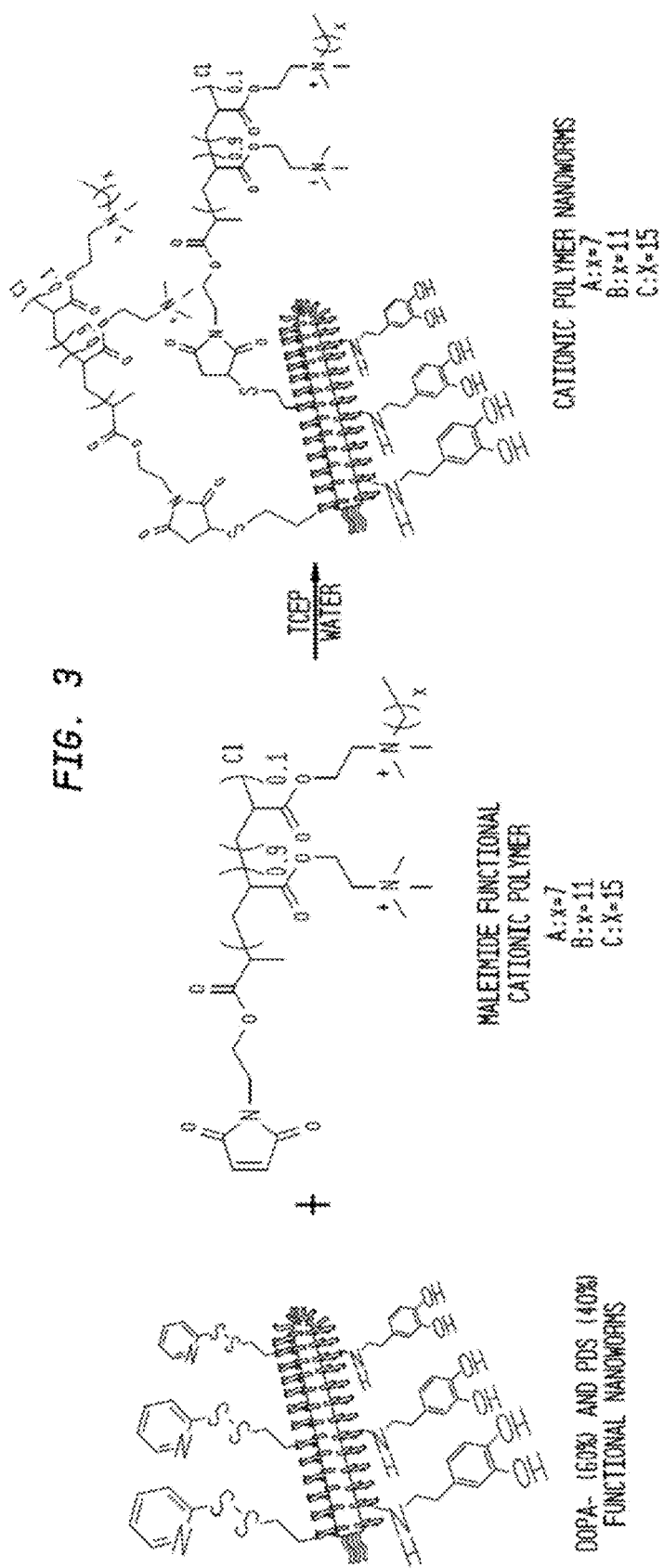

NANOWORM A

NANOWORM B

NANOWORM C

ANTIMICROBIAL COMPOUNDS AND NANOSTRUCTURES

CROSS-REFERENCE TO RELATED APPLICATIONS

This application is a U.S. non-provisional patent application that claims the benefit of a co-pending U.S. provisional patent application Ser. No. 62/521,040 filed Jun. 16, 2017. The aforementioned related patent application is incorporated herein by reference in its entirety.

FIELD

The present disclosure provides compounds and nanostructures having one or more quaternary ammonium salts, compositions including the compounds and nanostructures, and methods useful for treating conditions using the compounds, nanostructures, and compositions.

BACKGROUND

Preventing disease transmission on aircraft has conventionally focused on improvements of the air-conditioning/filtration systems. Recent research has suggested that one way to further improve disease prevention on aircraft and spacecraft can include surface contamination treatment, e.g. on surfaces of the aircraft. However, while some antimicrobial compounds have been produced for antibacterial applications, no compound has been demonstrated specifically for anti-viral applications. For antiviral compounds, the biotechnology and pharmaceutical industries use proteins and small molecules (e.g., molecular weight less than 1,000) to target microbes. However, proteins and small molecules have limited systemic half-lives and, in turn, typically involve higher dosages than is desired.

Furthermore, hydrophobic binding of existing antimicrobial materials requires long dehydration times before being effective such that a considerable amount of microbe transmission occurs during the dehydration, such that antimicrobial activity is not efficacious against strong microbes (such as Escherichia coli (E. Coli)).

Therefore, there is a need for antimicrobial compounds and nanostructures capable of further functionalization and antimicrobial activity against strong microbes (such as E. Coli), compositions including the compounds and nanostructures, and methods useful for antimicrobial and/or antiviral applications using the compounds, nanostructures, and compositions.

SUMMARY

The present disclosure provides compounds and nanostructures having one or more quaternary ammonium salts, compositions including the compounds and nanostructures, and methods useful for treating conditions (such as viruses and toxin-related conditions) using the compounds, nanostructures, and compositions.

At least one compound is represented by formula (I):

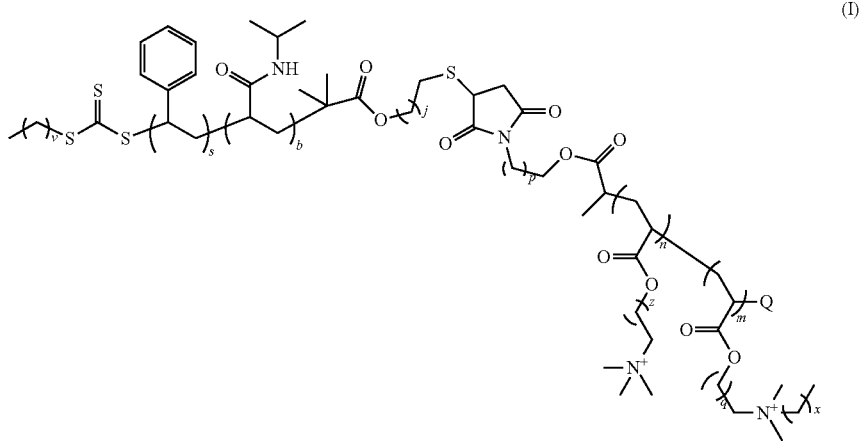

(I)

or a pharmaceutically acceptable salt thereof, wherein:
Q is fluoro, chloro, bromo, or iodo;
each of s, b, and n is independently an integer from about 10 to about 100; and
each of v, j, p, z, q, x and m is independently an integer from 1 to about 20.

At least one composition of the present disclosure includes a compound represented by formula (I), or a pharmaceutically acceptable salt thereof, and one or more additional components. The composition can have a three dimensional conformation that is a nanoworm or nanorod.

At least one method includes depositing a compound or composition of the present disclosure onto an object, such as an internal surface of an aircraft. At least one method includes a method for treating a condition comprising administering to a subject a therapeutically effective amount of a compound represented by formula (I), or a pharmaceutically acceptable salt thereof, (or a composition including a compound represented by formula (I), or a pharmaceutically acceptable salt thereof), wherein the condition to be treated includes viral infections, bacterial infections, chronic inflammatory disorders, acute inflammatory disorders, or cancer.

At least one method includes preparing a compound of formula (I), or pharmaceutically acceptable salt thereof. At least one method includes preparing a composition including a compound of formula (I), or pharmaceutically acceptable salt thereof.

BRIEF DESCRIPTION OF THE DRAWINGS

So that the manner in which the above recited features of the present disclosure can be understood in detail, a more particular description of the disclosure, briefly summarized above, may be had by reference to aspects, some of which are illustrated in the appended drawings. It is to be noted, however, that the appended drawings illustrate only typical aspects of this present disclosure and are therefore not to be considered limiting of its scope, for the present disclosure may admit to other equally effective aspects.

FIG. 2B is a $^1$H NMR spectrum of maleimide functional quaternized-poly-DMAEA in deuterated water, according to one aspect.

FIG. 2C is a $^1$H NMR spectrum of maleimide functional quaternized-poly-DMAEA in deuterated water, according to one aspect.

FIG. 3 is a scheme illustrating conjugation of maleimide functional cationic polymer to Dopa- and PDS-functional nanoworms, according to one aspect.

Figure 1:
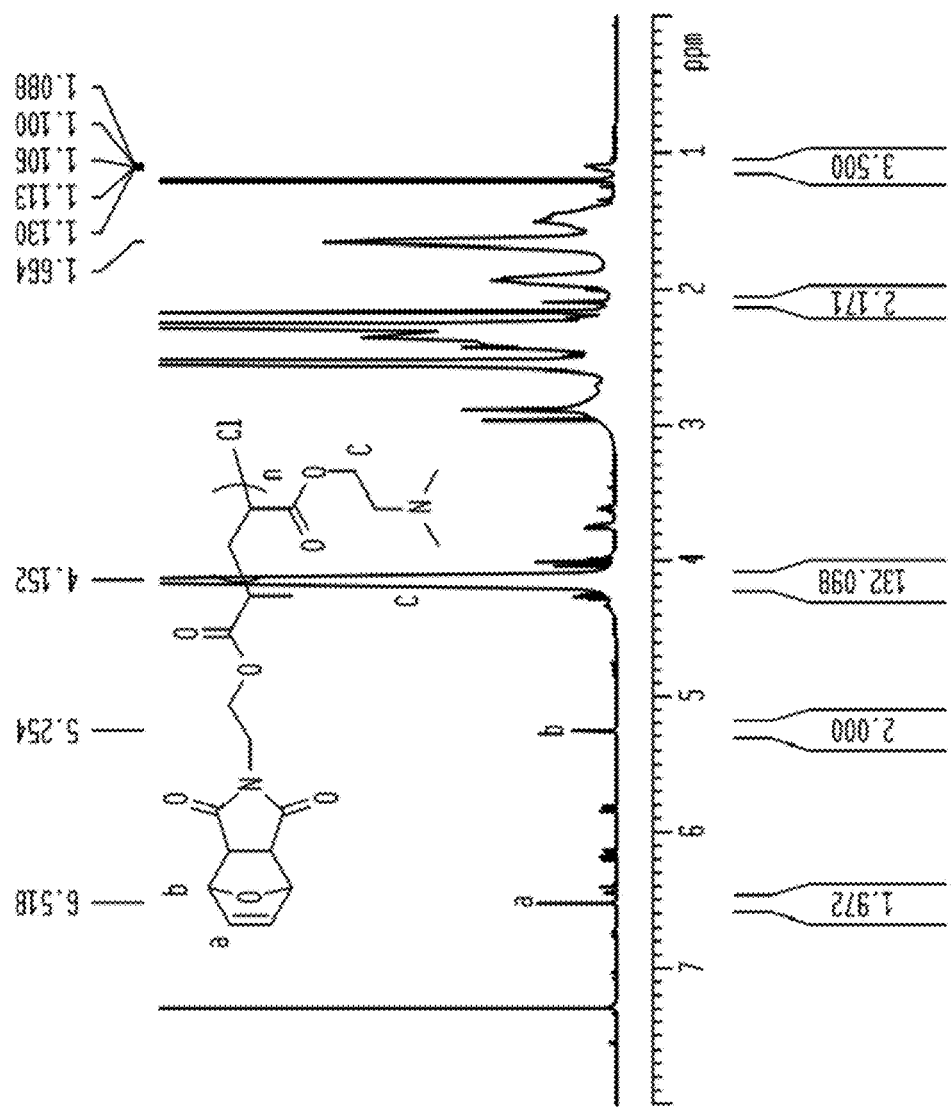
FIG. 1 is a $^1$H nuclear magnetic spectrum of the polymer in deuterated chloroform, according to one aspect.

To facilitate understanding, identical reference numerals have been used, where possible, to designate identical elements that are common to the figures. The figures are not drawn to scale and may be simplified for clarity. It is contemplated that elements and features of one aspect may be beneficially incorporated in other aspects without further recitation.

DETAILED DESCRIPTION

The present disclosure provides compounds and nanostructures having one or more quaternary ammonium salts, compositions including the compounds and nanostructures, and methods useful for treating conditions using the compounds, nanostructures, and compositions.

Compounds

In at least one aspect, a compound is represented by formula (I):

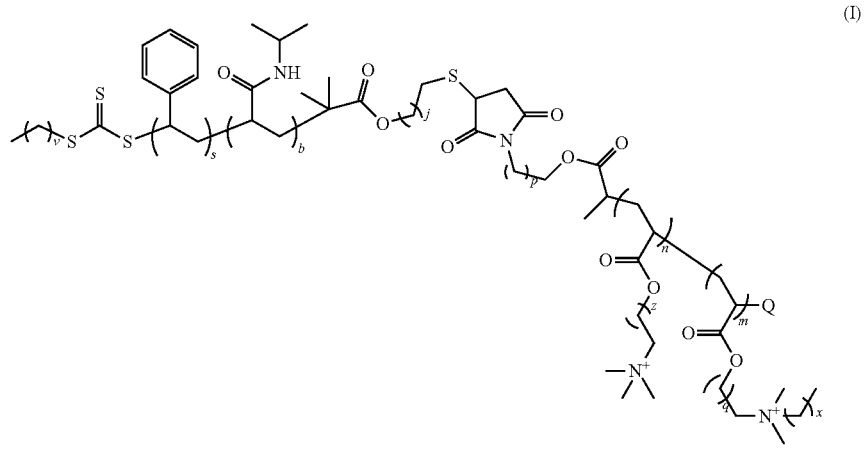

or a pharmaceutically acceptable salt thereof, where Q is fluoro, chloro, bromo, or iodo, preferably chloro;
each of s, b, and n is independently an integer from about 10 to about 100; and
each of v, j, p, z, q, x and m is independently an integer from 1 to about 20.

In at least one aspect, s is an integer from about 20 to about 40, such as about 25 to about 35. b can be an integer from about 30 to about 60, such as from about 40 to about 50. n can be an integer from about 30 to about 60, such as from about 50 to about 60. m can be an integer from about 1 to about 10, such as from about 5 to about 10. x can be an integer from about 5 to about 15, for example 7, 11, or 15.

Without being bound by theory, x values from about 5 to about 15 provide cell membrane penetration of the alkyl moiety into the hydrophobic portion of a cell membrane (such as a viral cell), while the cationic nitrogen moieties of the compound of formula (I) provide coulombic interactions of the compound of formula (I) (such as the quaternary ammonium moieties) with the cell membrane surface (such as the phosphate moieties of the phospholipid bilayer). Furthermore, the quaternary ammonium salt provides sufficient hydrophilicity so that the alkyl moieties attached to the quaternary ammonium salt do not become substantially buried within the core of the three dimensional structure (e.g., when the composition has the three dimensional structure of nanoworm or nanorod).

The polystyrene block of the compound of formula (I) can provide a high glass transition temperature (Tg) component to the compound of formula (I) (100% polystyrene has a Tg of about 100° C.). The high Tg provides stability to the nanostructures at body temperature. Furthermore, the poly (N-isopropylacrylamide) (poly-NIPAM) block can provide a nanoworm (or nanorod) three dimensional conformation of the compound of formula (I) under aqueous conditions, e.g. an aqueous solution containing sodium dodecyl sulfate (SDS).

The ratio of the integer n to the integer m can be selected to fine tune the coulombic binding ability versus cell membrane penetrating capability of a compound of formula (I). A higher integer n value provides increased coulombic binding, while a higher integer m provides increased cell membrane penetrating capability of a compound of formula (I). In at least one aspect, a ratio of the integer n to the integer m is from about 1:1 to about 100:1, such as from about 5:1 to about 15:1, for example 54:7.

The values of v, j, p, z, and q can be varied based on the number of, for example, methylene units of the starting materials used to form the compounds of formula (I). The value of s can be controlled by controlling the molar ratio of styrene monomers to NIPAM monomers and maleimide starting materials, as described in more detail below. Similarly, the value of b can be controlled by controlling the molar ratio of NIPAM monomers to styrene monomers and maleimide starting materials. The values of n and m can be controlled by the ratio of, for example, methyl halide to other alkyl halide (e.g., octyl halide) used to form the quaternary ammonium salt moieties.

In at least one aspect, the compound represented by formula (I) is represented by formula (II):

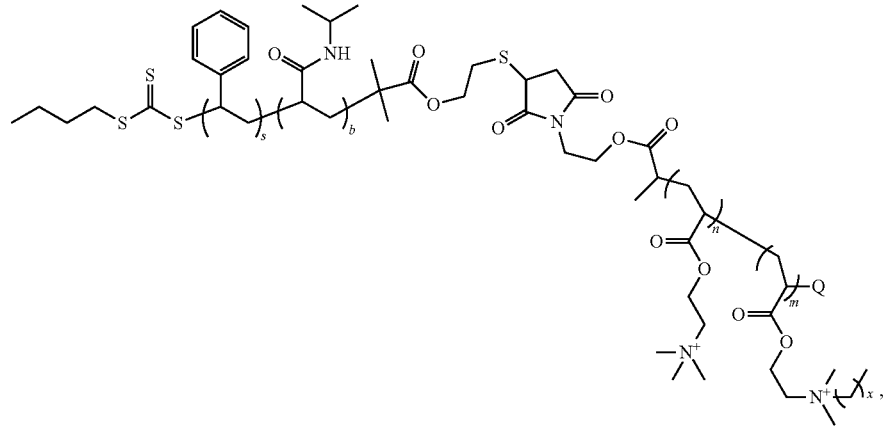

(II)

or a pharmaceutically acceptable salt thereof, where Q is fluoro, chloro, bromo, or iodo, preferably chloro;
each of s, b, and n is independently an integer from about 10 to about 100; and
each of x and m is independently an integer from 1 to about 20.

In at least one aspect, s of formula (II) is an integer from about 20 to about 40, such as from about 25 to about 35. b of formula (II) can be an integer from about 30 to about 60, such as from about 40 to about 50. n of formula (II) can be an integer from about 30 to about 60, such as from about 50 to about 60. m of formula (II) can be an integer from about 1 to about 10, such as from about 5 to about 10. x of formula (II) can be an integer from about 5 to about 15.

In at least one aspect, the compound represented by formula (I) or formula (II) is represented by formula (III):

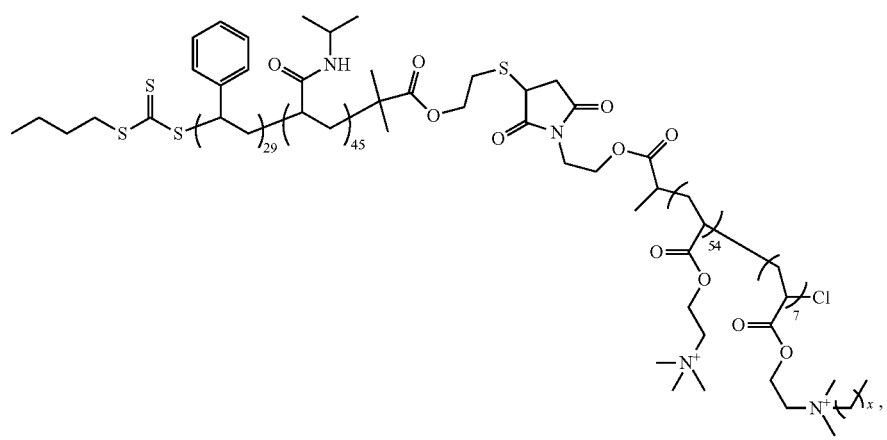

(III)

or a pharmaceutically acceptable salt thereof, where x is an integer from about 5 to about 15, for example 7, 11, or 15.

Compositions:

A compound represented by formula (I), formula (II), or formula (III), or a pharmaceutically acceptable salt thereof, can be present in a composition with one or more additional components. Additional components can include one or more pharmaceutically active compounds.

In at least one aspect, a composition includes a compound represented by formula (I):

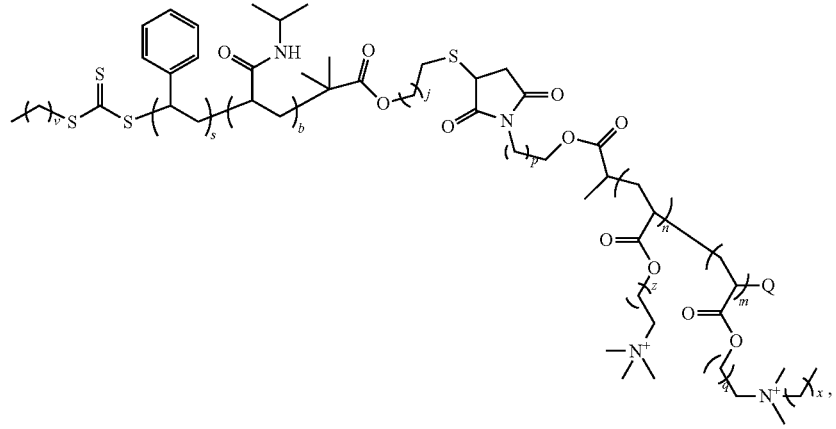

(I)

or a pharmaceutically acceptable salt thereof, where Q is fluoro, chloro, bromo, or iodo, preferably chloro;

each of s, b, and n is independently an integer from about 10 to about 100; and each of v, j, p, z, q, x and m is independently an integer from 1 to about 20.

In at least one aspect, s is an integer from about 20 to about 40, such as about 25 to about 35. b can be an integer from about 30 to about 60, such as from about 40 to about 50. n can be an integer from about 30 to about 60, such as from about 50 to about 60. m can be an integer from about 1 to about 10, such as from about 5 to about 10. x can be an integer from about 5 to about 15, for example 7, 11, or 15.

In at least one aspect, a ratio of the integer n to the integer m is from about 1:1 to about 100:1, such as from about 5:1 to about 15:1, for example 54:7.

In at least one aspect, the compound represented by formula (I) is represented by formula (II):

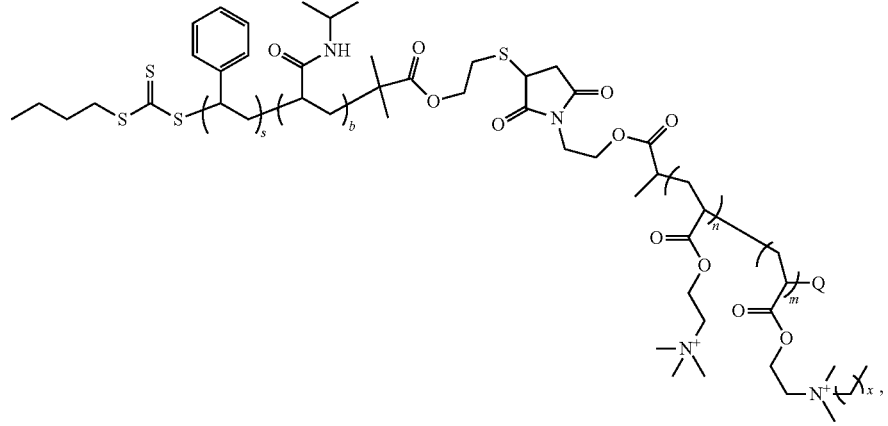

(II)

or a pharmaceutically acceptable salt thereof, where Q is fluoro, chloro, bromo, or iodo, preferably chloro;

each of s, b, and n is independently an integer from about 10 to about 100; and each of x and m is independently an integer from 1 to about 20.

In at least one aspect, s of formula (II) is an integer from about 20 to about 40, such as from about 25 to about 35. b of formula (II) can be an integer from about 30 to about 60, such as from about 40 to about 50. n of formula (II) can be an integer from about 30 to about 60, such as from about 50 to about 60. m of formula (II) can be an integer from about 1 to about 10, such as from about 5 to about 10. x of formula (II) can be an integer from about 5 to about 15.

In at least one aspect, the compound represented by formula (I) or formula (II) is represented by formula (III):

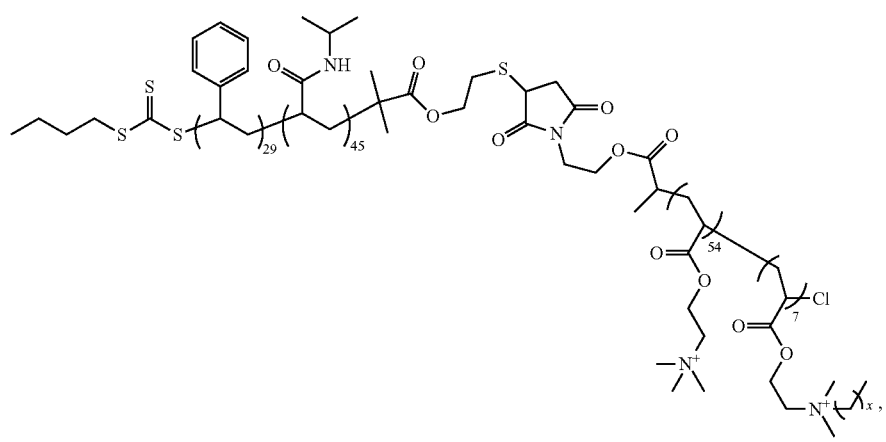

(III)

or a pharmaceutically acceptable salt thereof, where x is an integer from about 5 to about 15, for example 7, 11, or 15.

Compositions of the present disclosure can further include an additional component that is a compound represented by formula (IV):

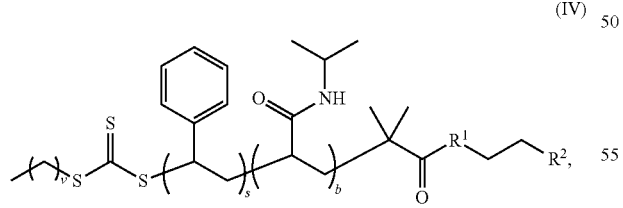

(IV)

or a pharmaceutically acceptable salt thereof, where each of s and b of formula (IV) is independently an integer from about 10 to about 100;

v of formula (IV) is an integer from about 1 to about 20;

$R^1$ is —O— or —NH—; and $R^2$ is —$CH_3$, biotin, pyridyl disulfide, dopa, thiolactone, or adamantyl. Biotin can be of the structure:

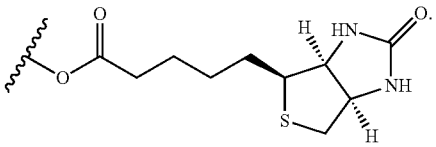 [SMILES: *OC(=O)CCCC[C@@H]1SC[C@@H]2NC(=O)N[C@@H]21]

Pyridyl disulfide can be of the structure:

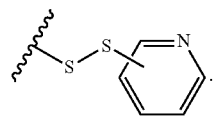

Dopa can be of the structure:

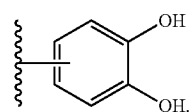

Thiolactone can be γ-thiolactone of the structure

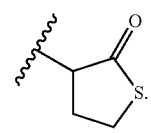 [SMILES: *C1CCSC1=O]

Adamantyl can be of the structure

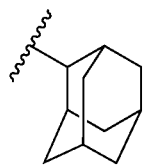

R² as pyridyl disulfide is particularly advantageous because it can be further conjugated to a pharmaceutically active moiety. Pharmaceutically active moieties include polymers, sugars, peptides, oligonucleotides, proteins, or small molecule (e.g., 2,000 g/mol or less) therapeutic drugs, such as an anticancer drug. Proteins include glycoproteins, such as Vitornectin. Small molecule therapeutic drugs include Relenza binders. Peptides include twin-arginine or translocation (TAT) peptide. Oligonucleotides include siRNA.

Furthermore, pyridyl disulfide can undergo thiol-disulfide exchange or thiolene reactions, Dopa can bind to a metal surface, γ-thiolactone can undergo an amination reaction (e.g., with an amino acid), biotin can bind to a biomolecule (e.g., streptavidin), and adamantly can be brominated, fluorinated, carboxylated, or hydroxylated.

In at least one aspect, s of formula (IV) is an integer from about 25 to about 35. b of formula (IV) can be an integer from about 40 to about 50. v of formula (IV) can be an integer from 1 to about 10, for example 2.

In at least one aspect, the compound represented by formula (IV) is one or more of the compounds represented by formula (V), formula (VI), or formula (VII), or pharmaceutically acceptable salts thereof,:

resented by formula (V), and an additional compound represented by formula (IV). A ratio of the compound represented by formula (I), (II), or (III) to the compound represented by formula (V) to the compound represented by formula (IV) is from about 0.99:0.005:0.005 to about 0.01: 0.09:0.009, such as from about 0.9:0.05:0.05 to about 0.1: 0.08:0.01, such as from about 0.8:0.1:0.1 to about 0.1:0.1: 0.8.

Three Dimensional Structures of a Compound or Composition

Long and flexible worms have in vivo blood circulation times about 10 times longer than their spherical analogues and have significantly longer circulation times than any synthetic particle or polyethylene oxide-coated vesicles. Short rods, on the other hand, have much shorter circulation times but are more efficiently taken up by cells.

Compounds or compositions of the present disclosure can have a 3-dimensional structure that is a nanoworm or nanorod. A nanorod can have an aspect ratio from about 10:1 to about 1000:1, such as from about 10:1 to about 100:1, such as from about 25:1 to about 75:1. A nanorod can have a diameter from about 10 nm to about 20 nm and a length from about 100 nm to about 10 microns, such as from about 1 micron to about 2 microns.

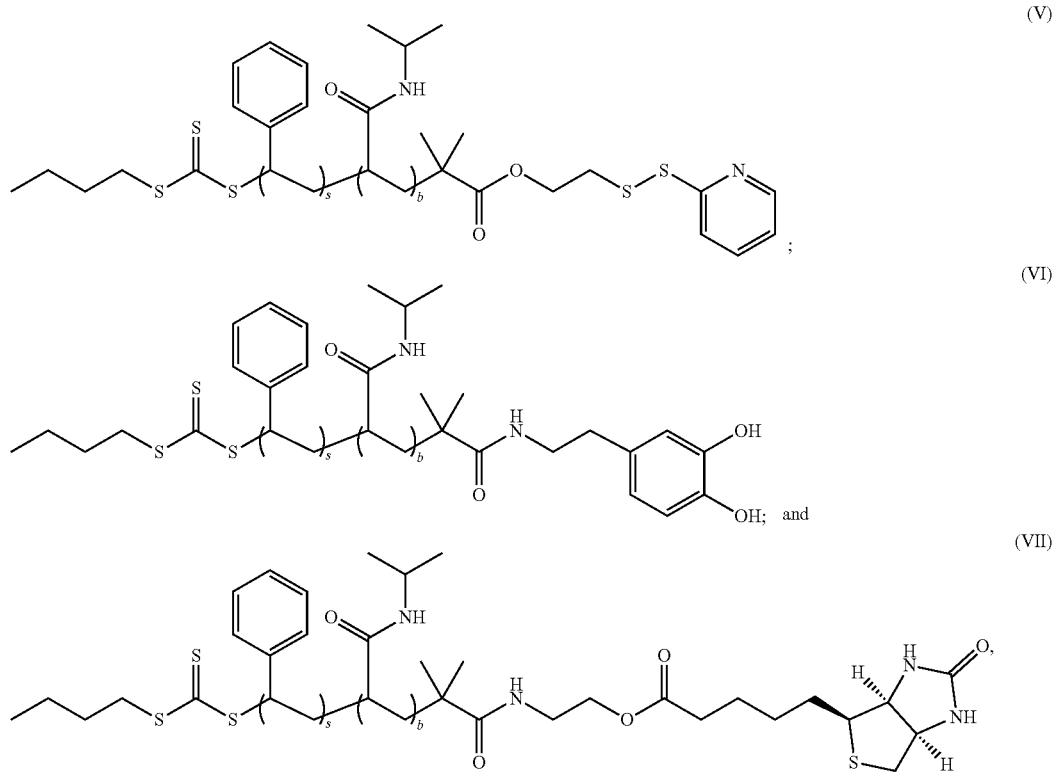

where s is an integer from about 25 to about 35 and b is an integer from about 40 to about 50.

In at least one aspect, a ratio of the compound represented by formula (I), (II), or (III) to the compound represented by formula (IV), formula (V), formula (VI), or formula (VII) is from about 0.01:1 to about 1:0.01.

In at least one aspect, a composition includes a compound represented by formula (I), (II), or (III), a compound rep- Compounds and compositions of the present disclosure can also have a three dimensional structure that is a sphere, vesicle, donut or lamella sheet. The three dimensional structure of compositions of the present disclosure can be stable in water for long periods of time (e.g., a nanoworm stable for a year or more at room temperature) and can also be freeze-dried and rehydrated without structural reorganization. For example, a nanoworm solution can be freeze-dried to give dry power. The freeze-dried product can be rehydrated in Milli-Q water at ~8 wt % for 2 h. The ability of a composition of the present disclosure to be freeze-dried provides stable transportation of compositions of the present disclosure.

Nanoworm Formation

Preparation of functional thermo-responsive polymer nanorods RAFT-mediated polymerization of styrene with functional poly(NIPAM) macro chain transfer agent (macroCTA) in water:

Precursor compounds (e.g., a compound represented by formula (I) but without the polystyrene block) can be mixed with styrene, sodium dodecyl sulfate, and azobisisobutyronitrile (AIBN) in water (such as Milli-Q water) to form a reaction mixture. One or more additional precursor compounds (e.g., a compound represented by formula (IV) but without the polystyrene block) can also be added to the reaction mixture.

AIBN can be dissolved in styrene followed by addition of the solution into a flask containing the other reaction components to form the reaction mixture. The solution of AIBN and styrene can be deoxygenated by purging with Argon for, for example, about 15 minutes. The reaction mixture can be purged with Argon for, for example, about 10 minutes in an ice bath before heating to 70° C. for about 3.5 hours to form a product mixture.

The number average molecular weight (Mn) of the compounds of formula (IV) in the product mixture is determined by nuclear magnetic resonance spectroscopy, unless stated otherwise. $^1$H NMR can be measured by freeze-drying the product mixture to remove all water and low boiling point compounds and then dissolving the product mixture in $CDCl_3$. A size exclusion chromatography spectrum can be obtained by taking 3 drops of latex and dissolving in 1 mL of THF, filtering and injecting the solution into the SEC apparatus.

Alternatively, conversion of styrene monomers can be determined by gravimetry. The theoretic molecular weights can be calculated based on the monomer conversions. The molecular weights ($M_{n(SEC)}$) and $PDI_{SEC}$ can be obtained by THF SEC. The molecular weights ($M_{n(NMR)}$) is obtained from $^1$H NMR. The particle size ($D_h$) and the particle size distribution ($PDI_{DLS}$) can be measured by dynamic light scattering (DLS) at 70° C. immediately after stopping the reaction, the results were the average value based on three measurements. $PDI_{DLS}<0.1$ means narrow distribution.

Nanoworms Cut into Nanorods using Ultrasound.

Nanorods can be obtained by temperature directed morphology transformation (TDTM) and ultrasound cutting of the nanoworms. In at least one aspect, a 6 mL latex solution of a nanoworm can be transferred to 2 hot vials (3 mL each) with 60 SL of toluene in each vials. These vials can then be sealed and shaken. The suspensions in these vials can be cooled to 23° C. The latex solutions can be cooled from 70° C. to 15° C. for about 30 min. The nanostructure can be characterized by transmission electron microscopy (TEM) to confirm the formation of worm-like nanostructures. To form the rods, the worms can be diluted by adding 10 mL of Milli-Q water, and cut using an ultrasound probe (with the pulse of 3 s on and 2 s off as one pulse cycle) for 3 min in an ice-bath at 35% amplitude (3 mm Tapered Micro Tip, VC-750 system from Sonics & Materials). After ultrasound cutting, the nanostructure can be characterized by TEM again to confirm the formation of rods.

Ultrasonic cutting of nanoworms to nanorods can also be carried out by applying probed ultrasound with different pulse cycles (15 seconds on and 10 seconds off as one pulse cycle), (B) 12 cycles (3 min), (C) 36 cycles (9 min) and (D) 48 cycles (12 min).

In at least one aspect, heating a nanoworm or nanorod composition of the present disclosure above the lower critical solution temperature (LCST) (about 37° C.) of the PNIPAM block can produce a gel that when cooled can dissociate back to a sol; a process that is reversible. Nanoworms can form gels at a minimum weight fraction of from about 1 wt % to about 8 wt % in an aqueous solution. Nanorods can form gels at a minimum weight fraction of from about 2 wt % to about 16 wt % in an aqueous solution. Without being bound by theory, gels are advantageous because they can be dissociated with increased temperature (such as from room temperature to body temperature of a subject, such as a human) to allow the worm 3-dimensional structure to dissociate and move through the blood.

The weight percentages of the nanorods in water at which the gel can be formed at 37 ° C. can be measured as follows: generally, the freeze-dried nanorods (e.g., 20 mg) can be redispersed in Milli-Q water by vortexing at 30 wt % in a 1.5 ml Eppendorf tube at 25° C. The tube can then be capped and immersed in a water bath at 37° C. for 2 min. The tube can then be flipped under the water bath to observe the gel formation. Gel formation is defined as no observable flowing of the fluid within 30 seconds. The weight percentage can be lowered by adding more Milli-Q water and vortexing. The gel formation can then be checked again. The minimum weight percentage of the nanorods, for example, in water to form the gel at 37° C. is defined as wt % to form the gel.

Preferred Method of Synthesizing Compounds of Formula (I)

A preferred method of synthesizing compounds represented by formula (I) is shown in Scheme 1. A pyridyl disulfide capped diblock copolymer is reacted with a maleimide capped quaternary ammonium polymer in the presence of tris(2-carboxyethyl)phosphine (TCEP) in water to form a compound represented by formula (I). The pyridyl disulfide capped diblock copolymer can be a compound represented by formula (IV) or (V) as a starting material to react with the maleimide capped quaternary ammonium polymer to form a compound represented by formula (I).

Scheme 1

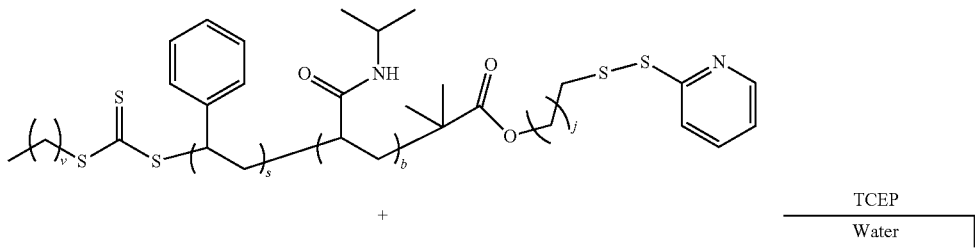

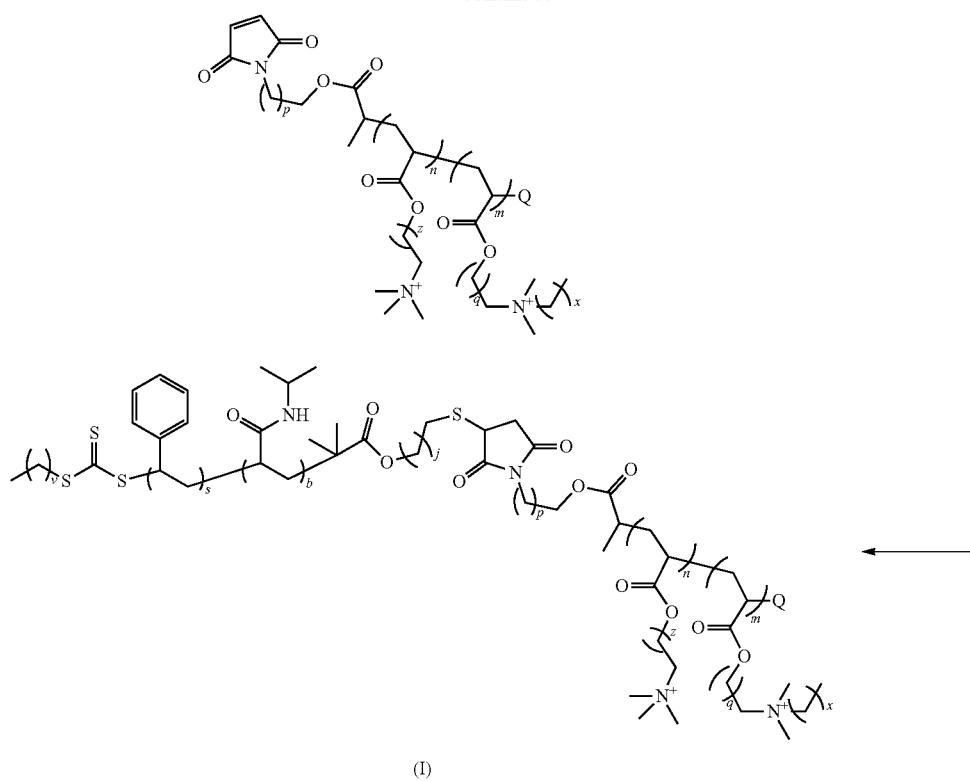

(I)

Methods for Depositing Compounds and Compositions

Compounds and compositions of the present disclosure may be deposited onto a surface of an object by any suitable deposition method. Deposition methods can include one or more of painting, dipping, spraying, marking, taping, brush coating, spin coating, roll coating, doctor-blade coating. Before deposition, a compound or composition of the present disclosure can be diluted in a solvent, such as water. After deposition, the solvent may then evaporate at room temperature forming a compound/composition layer on the object.

In at least one aspect, the object is an interior surface of an aircraft/spacecraft/boat or an air filter surface of an aircraft/spacecraft/boat, such as a surface of an air-conditioning or filtration system. The object can be a floor surface, seat surface, overhead bin surface, ceiling surface, door surface and/or door handle surface of the interior of an aircraft.

In at least one aspect, a compound or composition of the present disclosure is sprayed onto a surface of an object for from about 1 second to about 10 minutes, such as from about 30 seconds to about 2 minutes. In at least one aspect, a compound or composition is sprayed onto a surface of an object in an amount from about 1 mL to about 25 kL, such as from about 100 L to about 1 kL.

Compounds or compositions of the present disclosure disposed on an object prevents, reduces, and/or eliminates the presence of bacteria and viruses, which can prevent, reduce, and/or eliminate human contact with such bacteria and viruses.

Compositions comprising nanostructures (e.g., nanorods or nanoworms) of the present disclosure are advantageous to deposit onto a surface because, for example, an antibacterial and antiviral compound can be applied as a single layer, maintaining efficacy of both compounds. As mentioned above, applying compositions having, for example, a conventional antimicrobial compound can be applied to a surface to form a first layer on the surface. A composition having, for example, a conventional antiviral compound can be applied to the first layer to form a second layer. However, the second layer (the antiviral layer) would mask the antimicrobial first layer (hindering its antimicrobial capabilities).

Applying a composition having a nanostructure as a single layer also reduces cost and time of applying the compounds to a surface, as compared to application of two or more layers.

Methods for Use as a Pharmaceutical Drug

The present disclosure further provides methods for treating a condition in a subject having or susceptible to having such a condition, by administering to the subject a therapeutically-effective amount of one or more compounds or compositions as described above. In one aspect, the treatment is preventative treatment. In another aspect, the treatment is palliative treatment. In another aspect, the treatment is restorative treatment.

A method for treating a condition can include administering to a subject a therapeutically effective amount of a compound represented by formula (I), or pharmaceutically acceptable salt thereof (or a composition having a compound represented by formula (I), or pharmaceutically acceptable salt thereof).

1. Conditions

The conditions that can be treated in accordance with the present disclosure include, but are not limited to, conditions caused by a toxin (such as an antigen) and inflammatory disorders such as septic shock. The conditions that can be treated in accordance with the present disclosure include, but are not limited to viral infections, bacterial infections, chronic inflammatory disorders, acute inflammatory disorders, and cancers. Preferably, the condition to be treated includes a bacterial infection, a viral infection, or a cancer immunotherapy. Cancer immunotherapy can include cervical cancers such as those resulting from an infection of the cervix with human papillomavirus.

Viral infections can include those caused by ebola, influenza, SARS, Noro (gastro), or Zika. Viral infections can include viral respiratory infections (e.g., of the nose, throat, upper airways, or lungs) such as pneumonia, laryngotracheobronchitis, bronchiolitis. Viral infections can include viral gastrointestinal infections such as gastroenteritis caused by a norovirus or rotavirus. Viral infections can include viral liver infections such as hepatitis. Viral infections can include viral nervous system infections such as encephalitis caused by rabies or West Nile. Viral infections include warts and/or infections caused by human papilloma virus (HPV). Viral infections can include infections that cause cancer such as infections caused by Epstein-Barr virus, Hepatitis B, Hepatitis C, Herpesvirus 8, or Human papillomavirus. Symptoms of viral infections can include fever, muscle aches, coughing, sneezing, runny nose, headache, chills, diarrhea, vomiting, rash, or weakness.

Bacterial infections can include pneumonia, meningitis, food poisoning, and bacterial skin infections such as those caused by Staphylococcus or Streptococcus, cellulitis, folliculitis, impetigo, and boils. Bacterial infections (e.g., by food poisoning) can include infections caused by *Escherichia coli* (*E. coli*), Campylobacter jejuni, Clostridium botulinum, listeria monocytogenes, salmonella, and Vibrio. Bacterial infections can include bacterial meningitis, Otitis media, urinary tract infection, and respiratory tract infections such as sore throat, bronchitis, sinusitis, and pneumonia. Symptoms of bacterial infections can include nausea, vomiting, diarrhea, fever, chills, and abdominal pain.

In some aspects, the methods described herein are used to treat patients with disorders arising from dysregulated cytokine, enzymes and/or inflammatory mediator production, stability, secretion, posttranslational processing. Examples of cytokines that may be dysregulated include interleukins 1, 2, 6, 8, 10, 12, 17, 22 and 23 along with tumor necrosis factor alpha and interferons alpha, beta and gamma. Examples of inflammatory mediators that may be dysregulated include nitric oxide, prostaglandins and leukotrienes. Examples of enzymes include cyclo-oxygenase, nitric oxide synthase and matrixmetalloprotease.

Examples of inflammatory conditions relevant to the technology include, but are not limited to, sepsis, septic shock, endotoxic shock, exotoxin-induced toxic shock, gram negative sepsis, toxic shock syndrome. Inflammatory conditions can include those experienced by immunosuppressed individuals, and can also include "superbugs", including bacterial and viral strains resistant to current therapeutics.

2. Subjects

Suitable subjects to be treated according to the present disclosure include mammalian subjects. Mammals according to the present disclosure include, but are not limited to, human, canine, feline, bovine, caprine, equine, ovine, porcine, rodents, lagomorphs, primates, and the like, and encompass mammals in utero. Subjects may be of either gender and at any stage of development.

3. Administration and Dosing

Compounds or compositions of the present disclosure can be administered to a subject in a therapeutically effective amount.

Compounds or compositions of the present disclosure can be administered by any suitable route in the form of a pharmaceutical composition adapted to such a route, and in a dose effective for the treatment intended. An effective dosage is typically in the range of about 0.001 to about 100 mg per kg body weight per day, preferably about 0.01 to about 30 mg/kg/day, in single or divided doses. Depending on age, species and condition being treated, dosage levels below the lower limit of this range can be suitable. In other cases, still larger doses can be used without side effects. Larger doses can also be divided into several smaller doses, for administration throughout the day.

Pharmaceutical Compositions

For the treatment of the conditions referred to above, the compounds of described herein can be administered as follows:

Oral Administration

Compounds or compositions of the present disclosure can be administered orally, including by swallowing, so that the compound enters the gastrointestinal tract, or absorbed into the blood stream directly from the mouth (e.g., buccal or sublingual administration).

Suitable compositions for oral administration include solid formulations such as tablets, lozenges and capsules, which can contain liquids, gels, or powders. Compositions for oral administration may be formulated as immediate or modified release, including delayed or sustained release, optionally with enteric coating.

Liquid formulations can include solutions, syrups and suspensions, which can be used in soft or hard capsules. Such formulations can include a pharmaceutically acceptable carrier, for example, water, ethanol, polyethylene glycol, cellulose, or an oil. The formulation can also include one or more emulsifying agents and/or suspending agents.

In a tablet dosage form the amount of a compound of formula (I) present can be from about 0.05% to about 95% by weight, such as from about 2% to about 50% by weight of the dosage form. In addition, tablets may contain a disintegrant, comprising from about 0.5% to about 35% by weight, such as from about 2% to about 25% of the dosage form. Examples of disintegrants include methyl cellulose, sodium or calcium carboxymethyl cellulose, croscarmellose sodium, polyvinylpyrrolidone, hydroxypropyl cellulose, or starch.

Suitable lubricants, for use in a tablet, can be present in amounts from about 0.1% to about 5% by weight. Lubricants can include calcium, zinc or magnesium stearate, or sodium stearyl fumarate.

Suitable binders, for use in a tablet, include gelatin, polyethylene glycol, sugars, gums, starch, hydroxypropyl cellulose and the like. Suitable diluents, for use in a tablet, include mannitol, xylitol, lactose, dextrose, sucrose, sorbitol, or starch.

Suitable surface active agents and glidants, for use in a tablet, may be present in amounts from about 0.1% to about 3% by weight. Surface active agents and glidants can include polysorbate 80, sodium dodecyl sulfate, talc, or silicon dioxide.

Parenteral Administration

Compounds and compositions of the present disclosure can be administered directly into the blood stream, muscle, or internal organs. Suitable methods for parenteral administration can include intravenous, intra-muscular, subcutaneous intraarterial, intraperitoneal, intrathecal, or intracranial. Suitable devices for parenteral administration include injectors (including needle and needle-free injectors) and infusion methods.

Compositions for parenteral administration can be formulated as immediate or modified release, including delayed or sustained release.

Most parenteral formulations are aqueous solutions containing excipients, including salts, buffering agents and carbohydrates.

Parenteral formulations can also be prepared in a dehydrated form (e.g., by lyophilization) or as sterile non-aqueous solutions. These formulations can include water. Solubility-enhancing agents can also be used in preparation of parenteral solutions.

Topical Administration

Compounds and compositions of the present disclosure can be administered topically to the skin or transdermally. Formulations for this topical administration can include lotions, solutions, creams, gels, hydrogels, ointments, foams, implants, patches and the like. Pharmaceutically acceptable carriers for topical administration formulations can include water, alcohol, mineral oil, glycerin, polyethylene glycol and the like. Topical administration can be performed by electroporation, iontophoresis, or phonophoresis.

Compositions for topical administration can be formulated as immediate or modified release, including delayed or sustained release.

Combinations and Combination Therapy

The compounds and compositions of the present disclosure can be used, alone or in combination with other pharmaceutically active compounds, to treat conditions such as those previously described above. The compound(s)/composition(s) of the present disclosure and other pharmaceutically active compound(s) can be administered simultaneously (either in the same dosage form or in separate dosage forms) or sequentially. Accordingly, in one aspect, the present disclosure includes methods for treating a condition by administering to the subject a therapeutically-effective amount of one or more compounds of the present disclosure and one or more additional pharmaceutically active compounds.

In another aspect, there is provided a pharmaceutical composition comprising one or more compounds of the present disclosure, one or more additional pharmaceutically active compounds, and a pharmaceutically acceptable carrier.

In another aspect, the one or more additional pharmaceutically active compounds is one or more anti-inflammatory drugs, anti-atherosclerotic drugs, immunosuppressive drugs, immunomodulatory drugs, cytostatic drugs, anti-proliferative agents, angiogenesis inhibitors, kinase inhibitors, cytokine blockers, or inhibitors of cell adhesion molecules.

Compounds and compositions of the present disclosure can also be used in combination with other therapeutic reagents that are selected for their therapeutic value for the condition to be treated. In general, the compounds and compositions described herein and, in aspects where combinational therapy is employed, other agents do not have to be administered in the same pharmaceutical composition, and, because of different physical and chemical characteristics, are optionally administered by different routes. The initial administration is generally made according to established protocols, and then, based upon the observed effects, the dosage, modes of administration and times of administration subsequently modified. In certain instances, it is appropriate to administer a compound of formula (I) as described herein in combination with another therapeutic agent. By way of example only, if one of the side effects experienced by a patient upon receiving a compound of formula (I) is rash, then it is appropriate to administer an anti-histamine agent in combination with the initial therapeutic agent. Or, by way of example only, the therapeutic effectiveness of a compound of formula (I) is enhanced by administration of another therapeutic agent (which also includes a therapeutic regimen) that also has therapeutic benefit. Regardless of the disease, disorder or condition being treated, the overall benefit experienced by the patient is either simply additive of the two therapeutic agents or the patient experiences a synergistic benefit.

Therapeutically effective dosages vary when the drugs are used in treatment combinations. Methods for experimentally determining therapeutically effective dosages of drugs and other agents for use in combination treatment regimens are documented methodologies. Combination treatment further includes periodic treatments that start and stop at various times to assist with the clinical management of the patient. In any case, the multiple therapeutic agents (one of which is a compound of formula (I)) are administered in any order, or even simultaneously. If simultaneously, the multiple therapeutic agents are optionally provided in a single, unified form, or in multiple forms (by way of example only, either as a single pill or as two separate pills).

In some aspects, one of the therapeutic agents is given in multiple doses, or both are given as multiple doses. If not simultaneous, the timing between the multiple doses optionally varies from more than zero weeks to less than twelve weeks.

In addition, the combination methods, compositions and formulations are not to be limited to the use of only two agents, the use of multiple therapeutic combinations are also envisioned. It is understood that the dosage regimen to treat, prevent, or ameliorate the condition(s) for which relief is sought, is optionally modified in accordance with a variety of factors. These factors include the disorder from which the subject suffers, as well as the age, weight, sex, diet, and medical condition of the subject. Thus, the dosage regimen actually used can vary widely, in some aspects, and therefore can deviate from the dosage regimens set forth herein.

The pharmaceutical agents which make up the combination therapy disclosed herein are optionally a combined dosage form or in separate dosage forms intended for substantially simultaneous administration. The pharmaceutical agents that make up the combination therapy are optionally also administered sequentially, with either agent being administered by a regimen calling for two-step administration. The two-step administration regimen optionally calls for sequential administration of the active agents or spaced-apart administration of the separate active agents. The time period between the multiple administration steps ranges from, a few minutes to several hours, depending upon the properties of each pharmaceutical agent, such as potency, solubility, bioavailability, plasma half-life and kinetic profile of the pharmaceutical agent. Circadian variation of the target molecule concentration is optionally used to determine the optimal dose interval.

Compounds represented by formula (I) and a composition having a compound represented by formula (I) can be used (e.g., administered) in combination with drugs from the following classes: NSAIDs, immunosuppressive drugs, immunomodulatory drugs, cytostatic drugs, anti-proliferative agents, angiogenesis inhibitors, biological agents, steroids, vitamin D3 analogs, retinoids, other kinase inhibitors, cytokine blockers, corticosteroids and inhibitors of cell adhesion molecules. Where a subject is suffering from or at risk of suffering from atherosclerosis or a condition that is associated with atherosclerosis, a compound represented by formula (I) or a composition having a compound represented by formula (I) described herein is optionally used together with one or more agents or methods for treating atherosclerosis or a condition that is associated with atherosclerosis in any combination. Examples of therapeutic agents/treatments for treating atherosclerosis or a condition that is associated with atherosclerosis include, but are not limited to any of the following: torcetrapib, aspirin, niacin, HMG CoA reductase inhibitors (e.g., atorvastatin, fluvastatin, lovastatin, pravastatin, rosuvastatin and simvastatin), colesevelam, cholestyramine, colestipol, gemfibrozil, probucol and clofibrate.

Where a subject is suffering from or at risk of suffering from an inflammatory condition, a compound represented by formula (I) or a composition having a compound represented by formula (I) described herein is optionally used together with one or more agents or methods for treating an inflammatory condition in any combination. Examples of therapeutic agents/treatments for treating an autoimmune and/or inflammatory condition include, but are not limited to any of the following: corticosteroids, nonsteroidal antiinflammatory drugs (NSAID) (e.g. ibuprofen, naproxen, acetaminophen, aspirin, Fenoprofen (Nalfon), Flurbiprofen (Ansaid), Ketoprofen, Oxaprozin (Daypro), Diclofenac sodium (Voltaren), Diclofenac potassium (Cataflam), Etodolac (Lodine), Indomethacin (Indocin), Ketorolac (Toradol), Sulindac (Clinoril), Tolmetin (Tolectin), Meclofenamate (Meclomen), Mefenamic acid (Ponstel), Nabumetone (Relafen), Piroxicam (Feldene), cox-2 inhibitors (e.g., celecoxib (Celebrex))), immunosuppressants (e.g., methotrexate (Rheumatrex), leflunomide (Arava), azathioprine (Imuran), cyclosporine (Neoral, Sandimmune), tacrolimus and cyclophosphamide (Cytoxan), CD20 blockers (Rituximab), Tumor Necrosis Factor (TNF) blockers (e.g., etanercept (Enbrel), infliximab (Remicade) and adalimumab (Humira)), Abatacept (CTLA4-Ig) and interleukin-1 receptor antagonists (e.g. Anakinra (Kineret), interleukin 6 inhibitors (e.g., Actemra), interleukin 17 inhibitors (e.g., AIN457), Janus kinase inhibitors (e.g., Tasocitinib), syk inhibitors (e.g. R788), chloroquine and its derivatives.

For use in cancer and neoplastic diseases a compound represented by formula (I) or a composition having a compound represented by formula (I) described herein is optionally used together with one or more of the following classes of drugs: wherein the anti-cancer agent is an EGFR kinase inhibitor, MEK inhibitor, VEGFR inhibitor, anti-VEGFR2 antibody, KDR antibody, AKT inhibitor, PDK-1 inhibitor, PI3K inhibitor, c-kit/Kdr tyrosine kinase inhibitor, Bcr-Abl tyrosine kinase inhibitor, VEGFR2 inhibitor, PDGFR-beta inhibitor, KIT inhibitor, Flt3 tyrosine kinase inhibitor, PDGF receptor family inhibitor, Flt3 tyrosine kinase inhibitor, RET tyrosine kinase receptor family inhibitor, VEGF-3 receptor antagonist, Raf protein kinase family inhibitor, angiogenesis inhibitor, Erb2 inhibitor, mTOR inhibitor, IGF-1R antibody, NFkB inhibitor, proteosome inhibitor, chemotherapy agent, or glucose reduction agent.

Aspects

Clause 1. A compound represented by formula (I):

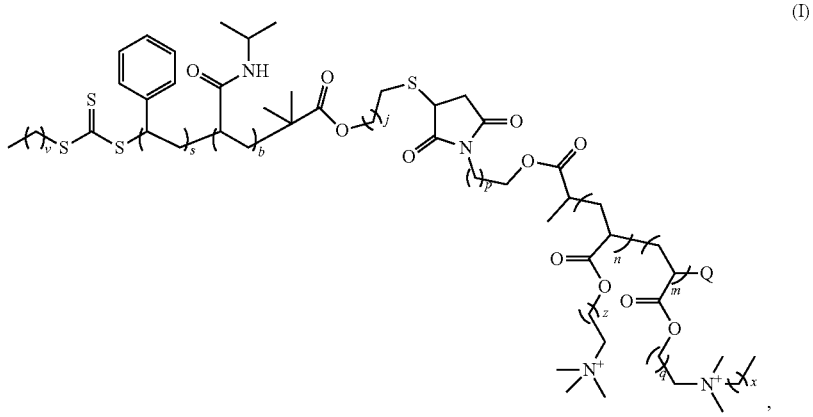

or a pharmaceutically acceptable salt thereof, wherein:
Q is fluoro, chloro, bromo, or iodo;
each of s, b, and n is independently an integer from about 10 to about 100; and
each of v, j, p, z, q, x and m is independently an integer from 1 to about 20.

Clause 2. The compound of clause 1, wherein s is an integer from about 20 to about 40.

Clause 3. The compound of clauses 1 or 2, wherein s is an integer from about 25 to about 35.

Clause 4. The compound of any of clauses 1-3, wherein b is an integer from about 30 to about 60.

Clause 5. The compound of any of clauses 1-4, wherein b is an integer from about 40 to about 50.

Clause 6. The compound of any of clauses 1-5, wherein n is an integer from about 30 to about 60.

Clause 7. The compound of any of clauses 1-6, wherein n is an integer from about 50 to about 60.

Clause 8. The compound of any of clauses 1-7, wherein m is an integer from about 1 to about 10.

Clause 9. The compound of any of clauses 1-8, wherein m is an integer from about 5 to about 10.

Clause 10. The compound of any of clauses 1-9, wherein Q is chloro.

Clause 11. The compound of any of clauses 1-10, wherein x is an integer from about 5 to about 15.

Clause 12. The compound of any of clauses 1-11, wherein x is the integer 7, 11, or 15.

Clause 13. The compound of any of clauses 1-12, wherein a ratio of the integer n to the integer m is from about 1:1 to about 100:1.

Clause 14. The compound of any of clauses 1-13, wherein the ratio of the integer n to the integer m is from about 5:1 to about 15:1.

Clause 15. The compound of any of clauses 1-14, wherein the compound is represented by formula (II):

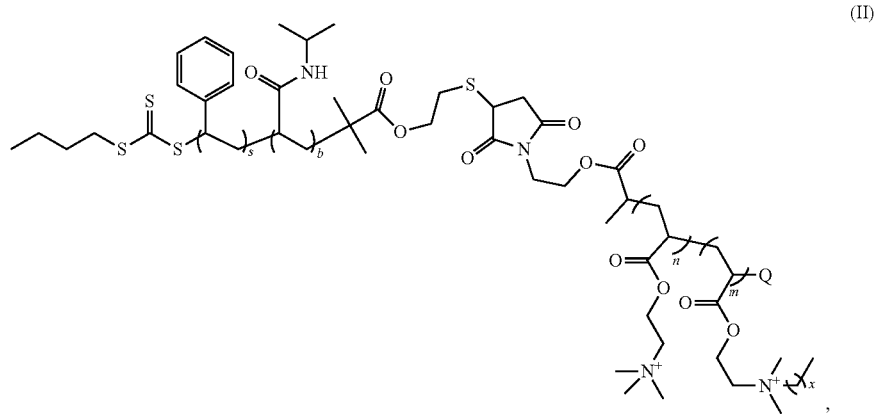

(II)

or a pharmaceutically acceptable salt thereof, wherein:
Q is fluoro, chloro, bromo, or iodo;
each of s, b, and n is independently an integer from about 10 to about 100; and
each of x and m is independently an integer from 1 to about 20.
Clause 16. The compound of clause 15, wherein s of formula (II) is an integer from about 20 to about 40.
Clause 17. The compound of clauses 15 or 16, wherein s of formula (II) is an integer from about 25 to about 35.
Clause 18. The compound of any of clauses 15-17, wherein b of formula (II) is an integer from about 30 to about 60.
Clause 19. The compound of any of clauses 15-18, wherein b of formula (II) is an integer from about 40 to about 50.

Clause 20. The compound of any of clauses 15-19, wherein n of formula (II) is an integer from about 30 to about 60.
Clause 21. The compound of any of clauses 15-20, wherein n of formula (II) is an integer from about 50 to about 60.
Clause 22. The compound of any of clauses 15-21, wherein m of formula (II) is an integer from about 1 to about 10.
Clause 23. The compound of any of clauses 15-22, wherein m of formula (II) is an integer from about 5 to about 10.
Clause 24. The compound of any of clauses 15-23, wherein Q is chloro.
Clause 25. The compound of any of clauses 15-24, wherein x of formula (II) is an integer from about 5 to about 15.
Clause 26. The compound of any of clauses 15-25, wherein the compound is represented by formula (III):

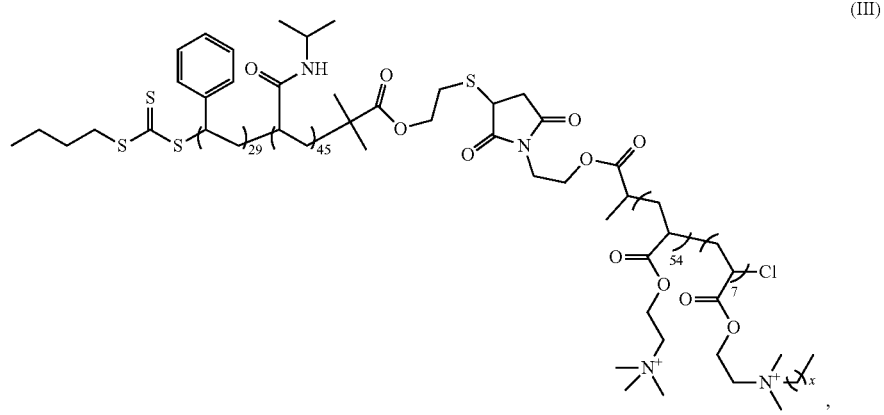

(III)

or a pharmaceutically acceptable salt thereof, wherein x is an integer from about 5 to about 15.

Clause 27. The compound of any of clauses 15-26, wherein x is the integer 7, 11, or 15.

Clause 28. A composition comprising:
  the compound of any of clauses 15-27; and
  a compound represented by formula (IV):

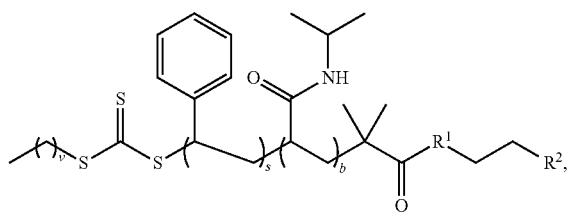

(IV)

or a pharmaceutically acceptable salt thereof, wherein:
each of s and b of formula (IV) is independently an integer from about 10 to about 100;
v of formula (IV) is an integer from about 1 to about 20;
$R^1$ is —O— or —NH—; and
$R^2$ is —CH$_3$, biotin, pyridyl disulfide, dopa, thiolactone, or adamantyl.

Clause 29. The composition of clause 28, wherein s of formula (IV) is an integer from about 25 to about 35.

Clause 30. The composition of clauses 28 or 29, wherein b of formula (IV) is an integer from about 40 to about 50.

Clause 31. The composition of any of clauses 28-30, wherein v of formula (IV) is 2.

Clause 32. The composition of any of clauses 28-31, wherein $R^2$ is

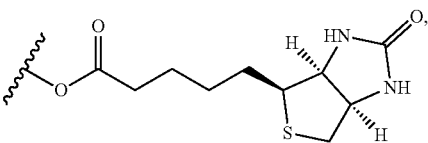

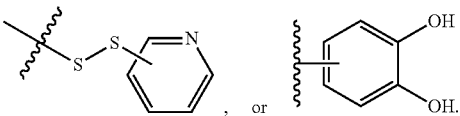, or 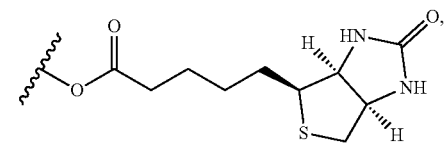

Clause 33. The composition of any of clauses 28-32, wherein the compound represented by formula (IV) is one or more of:

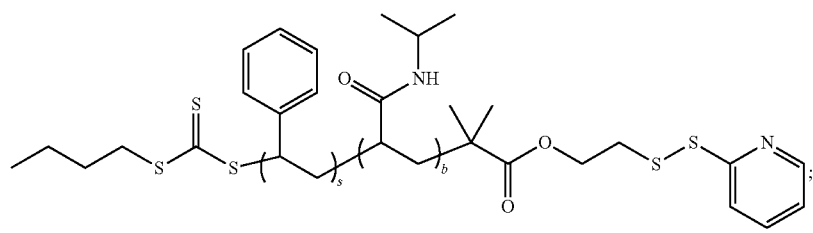;

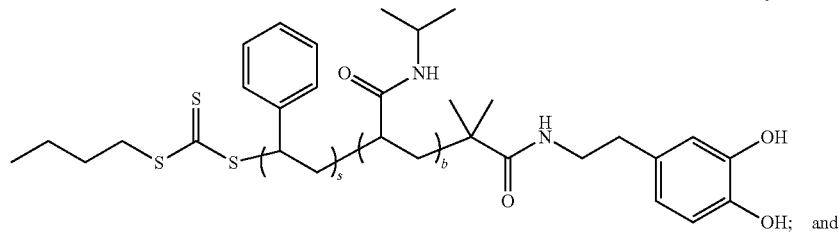; and

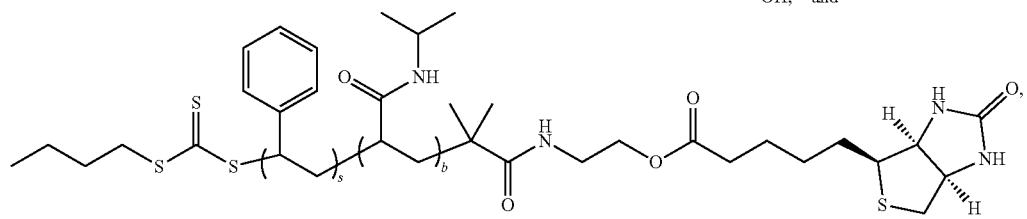

wherein s of formula (IV) is an integer from about 25 to about 35 and b of formula (IV) is an integer from about 40 to about 50.

Clause 34. The composition of any of clauses 28-33, wherein the composition has a 3-dimensional structure that is a nanoworm or nanorod.

Clause 35. The composition of any of clauses 28-34, wherein the composition is a nanorod having an aspect ratio from about 10:1 to about 1000:1.

Clause 36. The composition of any of clauses 28-35, wherein the composition is a nanorod having a diameter from about 10 nm to about 20 nm and a length from about 1 micron to about 2 microns.

Clause 37. The composition of any of clauses 28-36, wherein a ratio of the compound represented by formula (I) to the compound represented by formula (IV) is from about 0.01:1 to about 1:0.01.

EXAMPLES

Experimental:
Measurements

Nuclear Magnetic Resonance (NMR). All NMR spectra were recorded on a Bruker DRX 400 or 500 MHz spectrometer using an external lock (CDCl3 or DMSO-d6) and referenced to the residual nondeuterated solvent (CHCl$_3$ or DMSO).

Size Exclusion Chromatography (SEC) and Triple Detection-Size Exclusion Chromatography (TD-SEC). Analysis of the molecular weight distributions of the polymers were determined using a Polymer Laboratories GPC50 Plus equipped with differential refractive index detector. Absolute molecular weights of polymers were determined using a Polymer Laboratories GPC50 Plus equipped with dual angle laser light scattering detector, viscometer, and differential refractive index detector. High performance liquid chromatography (HPLC) grade N,N-dimethylacetamide (DMAc, containing 0.03 wt % LiCl) was used as the eluent at a flow rate of 1.0 mL/min. Separations were achieved using two PLGel Mixed B (7.8×300 mm) SEC columns connected in series and held at a constant temperature of 50° C. The triple detection system was calibrated using a 5 mg/mL 110 K polystyrene (PSTY) standard. Samples of known concentration were freshly prepared in DMAc+0.03 wt % LiCl and passed through a 0.45 μm PTFE syringe filter prior to injection. The absolute molecular weights and do/dc values were determined using Polymer Laboratories Multi Cirrus software based on the quantitative mass recovery technique.

Transmission Electron Microscopy (TEM). The nanostructure appearance of the polymer lattices was analyzed using a JEOL-1010 transmission electron microscope utilizing an accelerating voltage of 100 kV with spot size 5 at ambient temperature. A typical TEM grid preparation was as follows: the nanostructure samples were diluted with Milli-Q water at 34° C. to approximately 0.05 wt %. A formvar preheated (34° C.) copper TEM grid was then dipped in the diluted solution, blotted the excess solution by filter paper and then dried at 34° C.

Matrix Assisted Laser Desorption Ionisation Time of Flight Mass Spectroscopy (MALDI-TOF). A Mass Spectrometry Spectrum was recorded using a Bruker autoflex III smartbeam operated in reflection mode. Ions were accelerated at a potential of 20 kV with a nitrogen laser emitting at 337 nm. The polymer solution concentrations were 1 mg/mL in tetrahydrofuran (THF), for sodium trifluoroacetate (NaTFA) 1 mg/mL in THF and for DCTB (T-2-(3-(4-t-Butyl-phenyl)-2-methyl-2-propenylidene) malononitrile) 10 mg/ml. To prepare the sample for measurement, 20 μL polymer solution, 20 μL DCTB solutions and 2 μL NaTFA solution were mixed in an Eppendorf tube, vortexed and centrifuged. 1 μL solution was placed on the sample plate spot, dried at ambient condition and then proceeded the measurement.

UV-Vis spectrometer. UV-Vis absorption spectra were recorded on a UV-Vis Cary 4000 spectrophotometer at 25° C.

Confocal Microscopy. The confocal microscopy images of the fluorescence probe labeled nanorods were dispersed in Milli-Q water at 20 mg/mL. 5 SL of each sample was dropped on a glass slide. Confocal microscopy images were taken using a Confocal LSM Zeiss 710 Laser Scanning Microscope (inverted) with an oil-immersion objective (1.40 Oil DIC M27/63x). Two excitation wavelengths at 488 and 561 nm were used for Oregon green 488 and SAv-DyLight 550, respectively.

Dynamic Light Scattering (DLS). Dynamic Light Scattering measurements were performed using a Malvern Zetasizer Nano Series 3000HS running DTS software operating a 4 mW He-Ne laser at 633 nm. Analysis was performed at an angle of 173°. The sample refractive index (RI) was set at 1.59 for polystyrene. The dispersant viscosity and RI for water were set to 0.4071 mP (70° C.) and 1.33 Ns/m2, respectively. The number average hydrodynamic particle size and particle size distribution (PSD) were reported. The PSD was used to describe the width of the particle size distribution. It was calculated from a cumulate analysis of the DLS measured intensity autocorrelation function and related to the standard deviation of the hypothetical Gaussian distribution (i.e., $PSDDLS=\sigma^2/ZD^2$, where σ is the standard deviation and ZD is the Z average mean size).

For determination of the lower critical solution temperature (LCST) of all PNIPAM MacroCTAs, the polymer MacroCTAs were dissolved in Milli-Q water in an ice bath at a concentration of 5 mg/mL or 53.8 mg/mL, and SDS was added at a concentration of 0.21 mg/mL or 2.23 mg/mL, respectively. The solution was then filtered using a 0.45 μm cellulose syringe filter directly into a DLS cuvette. The polymer solution was cooled to 5° C. and the cuvette placed in DLS spectrometer. The measurement was carried out by slowly increasing the temperature from 5 to 70° C. at a ramp rate controlled by the SOP (standard operating procedure) software.

Materials:
Synthesis of Functional Polymer Nanostructure Materials

Unless otherwise stated, all chemicals were used as received. The solvents used were of either HPLC or AR grade; these included dichloromethane (DCM; Aldrich AR grade), dimethylformamide (DMF; Aldrich, AR grade) and tetrahydrofuran (THF; Labscan, HPLC grade), DMSO (Aldrich, 99.9%). Activated basic alumina (Aldrich: Brockmann I, standard grade, ~150 mesh, 58 A), Milli-Q water (Biolab, 18.2 M=m), sodium dodecyl sulphate (SDS; Aldrich, 99%), triethylamine (TEA; Fluka, 99%), N,N'-dicyclohexylcarbodiimide (DCC, Aldrich, 99%), N-hydroxysuccinimide (NHS, Aldrich, 98%), ethanolamine (Aldrich, >99%), 4-(dimethylamino)pyridine (DMAP, Merck, 99%), copper(II) sulfate (Aldrich, 99%), L-ascorbic acid (Aldrich, 99%), 1-butanethiol (Aldrich, 99%), propargyl alcohol (Aldrich, 99%), sodium azide (Aldrich, 99.5%), methacryloyl chloride (Fluka, 97%), 3-chloro-1-propanol (Aldrich, 98%), poly(ethylene glycol) mono methyoxyl ether-2000 (mPEG, Aldrich), p-toluenesulfonyl chloride (Aldrich, >99%), β-cyclodextrin (Sigma, >97%), allylamine (Aldrich, 98%), Aldrithiol™-2 (DPDS, Aldrich, 98%), 2-mercaptoethanol (Merck, >98%), dopamine hydrochloride (Sigma), DL-homocysteine thiolactone hydrochloride (TIa, Aldrich, >99%), biotin (Sigmal-Aldrich, >99%), N-(3-dimethylaminopropyl)-N'-ethylcarbodiimide hydrochloride (EDC.HCl, Fluka, >98%), L-glutathione reduced (Sigma-Aldrich, >98%), streptavidin from Streptomyces avidinii (SAv, Sigma), streptavidin DyLight 550 conjugated (Pierce), Oregon GreenR 488 maleimide (Molecular ProbesR), carbon disulfide (Aldrich, >99.9%), 2-bromo-2-methylpropionic acid (Aldrich, 98%) and methyl-2- bromopropionate (MBP; Aldrich, 98%) were used as received. Styrene (STY: Aldrich, >99%) was passed through a basic alumina column to remove inhibitor. N-isopropylacrylamide (NIPAM: Aldrich, 97%) was recrystallized from (n-hexane/toluene, 9/1, v/v), and azobisisobutyronitrile (AIBN, Riedel-de Haen) was recrystallized from methanol twice prior to use.

RAFT agent methyl 2-(butylthiocarbonothioylthio)propanoate (MCEBTTC) was synthesized according to the previous procedure. (C. N. Urbani, M. J. Monteiro, Macromolecules, 2009, 42, 3884-3886.)

Synthesis of Carboxylic Acid Functional RAFT Agent (Acid-RAFT)

Potassium phosphate tribasic (16.6 g, 0.0782 mol) was dissolved in 130 mL acetone in a 500 mL round bottom flask. This mixture was kept stirring for 5 h to make a light yellow suspension. To this mixture, 1-butanethiol (8.0 mL, 0.0742 mol) was added and stirred for 1h. Carbon disulfide (9.1 mL, 0.151 mol) was then added dropwise to this stirred mixture and stirred for 2 h at 0.5° C. (in an ice bath). 2-Bromo-2 methylpropionic acid (11.7 g, 0.07 mol) was added to the mixture under stirring, and the mixture was allowed to react overnight at room temperature (23° C.). The solid was isolated by filtration, and the solvent volume reduced by using rotary evaporation. The residue was then diluted by cold 10% HCl solution (4×50 mL) and stirred at room temperature overnight. This solution was then extracted twice with n-Hexane, dried over anhydrous MgSO$_4$, filtered, and solvent removed by rotary evaporation. The residual yellow solid was purified by column chromatography (petroleum spirit/ethyl acetate: 3/2 on silica, Rf=0.51). The solvent was then removed by rotary evaporation, the compound dissolved in n-Hexane, and kept in a freezer to crystallize. The product was filtered, dried under high vacuum for 24 h, producing a yield of 61%. $^1$H NMR (CDCl$_3$, 298K, 300 MHz): ppm 3.27 (t, 2H; J=7.38 Hz; CH$_3$CH$_2$CH$_2$CH$_2$S—), 1.70 (s, 6H; (CH$_3$)$_2$—), 1.64 (m, 2H, J=8.94 Hz; CH$_3$CH$_2$CH$_2$CH$_2$S—), 1.41 (m, 2H; J=7.29 Hz; CH$_3$CH$_2$CH$_2$CH$_2$S—), 0.90 (t, 3H, J=7.26 Hz; CH$_3$CH$_2$CH$_2$CH$_2$S—); 13C NMR (CDCl$_3$, 298K, 75 MHz): 228.3, 128.9, 55.6, 36.7, 29.8, 25.2, 22.1, 13.6.

Synthesis of Pyridyl Disulfide Functional RAFT Agent (PDS-RAFT)

As shown in Scheme 2, RAFT-acid (2.52 g, 0.01 mol), hydroxyethyl pyridyldisulfide (2.0 g, 0.011 mol), DCC (4.12 g, 0.02 mol) and DMAP (0.112 g, 9.18 ×10-4 mol) were dissolved in 50 mL of DCM which was cooled to 0° C. with an ice bath. The reaction mixture was allowed to warm to room temperature and stirred for 24 h. DCM was removed by rotary evaporation. The residue was redispersed in diethyl ether, filtered. The filtrate was concentrated to a viscous residual and purified by silica column chromatography (1/4 petroleum spirit/ethyl acetate), yield: 59.4%.

Scheme 2

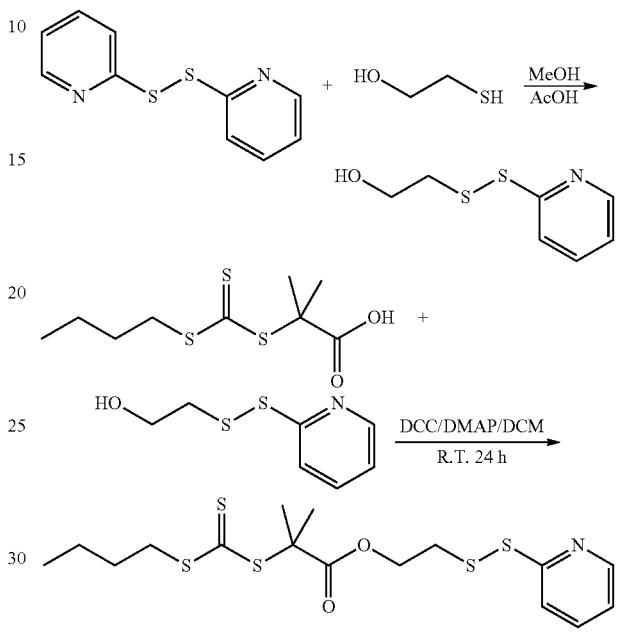

Synthesis of Dopamine Functional RAFT Agent (Dopa-RAFT)

As shown in Scheme 3, RAFT-acid (3.0 g, 0.012 mol), NHS (1.5 g, 0.013 mol) and DCC (2.67 g, 0.013 mol) were dissolved in 50 mL of DCM which was cooled to 0° C. with an ice bath. The reaction mixture was warmed up to room temperature and stirred for 2 h. The reaction was monitored by TLC to get full conversion to RAFT-active ester. The mixture was then filtered to another round bottom flask with stirrer. Dopamine hydrochloride (2.0 g, 0.011 mol) and TEA (1.7 mL, 0.012 mol) were dissolved in 10 mL DMF and added to the above RAFT-active ester dropwise. The reaction mixture was stirred for another 24 h. The color of reaction mixture turned brown. 50 mL of DCM was added to the reaction mixture. The mixture was then washed with 0.1N HCl solution followed by Milli-Q water. The color of the DCM phase turned to yellow. The DCM phase was dried over MgSO$_4$, filtered and concentrated. The filtrate was concentrated to a viscous residual and purified by silica column chromatography (1/1 petroleum spirit/ethyl acetate), yield: 44.3%.

Scheme 3

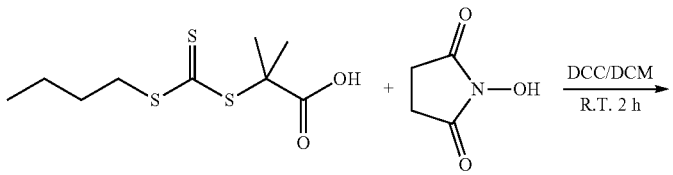

-continued

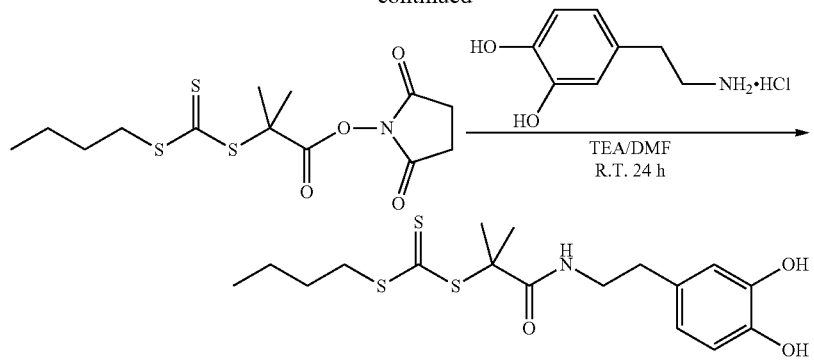

Synthesis of Biotin Functional RAFT Agent (Biotin-RAFT)
Synthesis of Hydroxyl Functional RAFT (RAFT-OH)

As shown in Scheme 4, RAFT-acid (1.75 g, 6.9×10-3 mol), NHS (0.95 g, 8.3×10-3 mol) and DCC (1.72 g, 8.3×10-3 mol) were dissolved in 30 mL of DCM which was cooled to 0° C. with an ice bath. The reaction mixture was warmed up to room temperature and stirred for 2 h. The reaction was monitored by TLC to get full conversion to RAFT-active ester. The mixture was then filtered to another round bottom flask with stirrer. Ethanolamine (0.4 g, 6.5×10-3 mol) was dissolved in 10 mL DMF and added to the above RAFT-active ester dropwise. The reaction mixture was stirred for another 24 h. The mixture was filtered, concentrated to a viscous residual and purified by silica column chromatography (1/2 petroleum spirit/ethyl acetate), yield: 55.0%.

Scheme 4

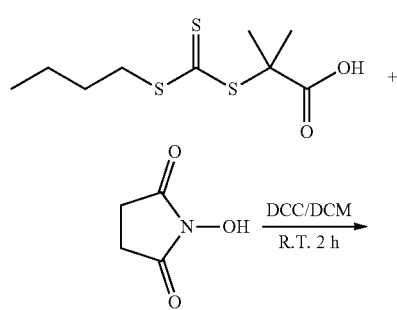

-continued

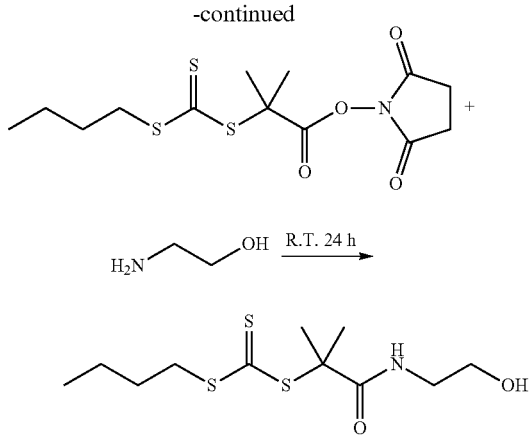

Synthesis of Biotin Functional RAFT (Biotin-RAFT)

As shown in Scheme 5, RAFT-OH (1.10 g, 3.73×10-3 mol), biotin (0.91 g, 3.73×10-3 mol), EDC.HCl (1.42 g, 7.45×10-3 mol) and DMAP (45.5 mg, 3.73×10-3 mol) were dissolved in 20 mL of DMF which was cooled to 0° C. with an ice bath. The reaction mixture was warmed up to room temperature and stirred for 48 h. The reaction mixture was then diluted with 100 mL DCM and washed by deionized water for five times. The DCM phase was then dried over MgSO$_4$, filtered, concentrated to a viscous residual and purified by silica column chromatography (1/8 methanol/DCM), yield: 69.6%.

Scheme 5

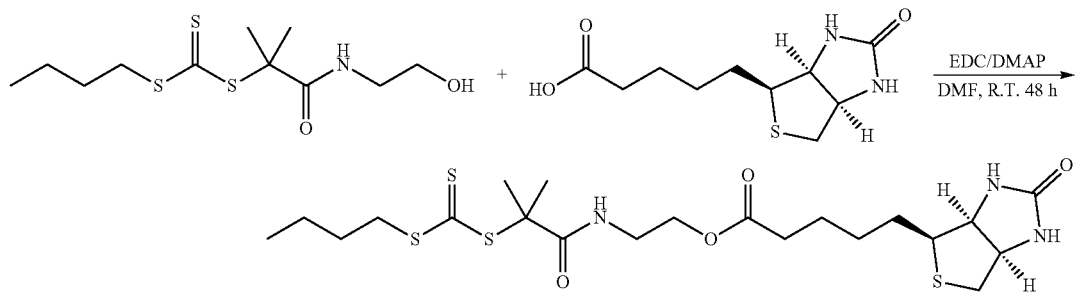

Synthesis of Functional Poly(NIPAM) Macro-CTA

All the functional poly(NIPAM) macro-CTAs were synthesized by reversible addition-fragmentation chain-transfer polymerization (RAFT polymerization) in DMSO at 60 °C. The feeding ratio of NIPAM/RAFT agent/AIBN was kept as 44/1/0.1 for all the different functional RAFT agents. The ratio of DMSO to NIPAM was kept as 2/1 (v/w). Typically, (10 g, 8.85×10-2 mol), methyl-RAFT (0.58 g, 2.0×10-3 mol) and AIBN (3.3 mg, 2.0×10-4 mol) were dissolved in 20 mL of DMSO. The mixture was purged with Argon for 30 min then heated at 60° C. for 16h. The reaction was stopped by cooling to 0° C. in an ice bath and exposed to air. The solution was then diluted with 500 mL of DCM and washed with Milli-Q water (5 x 100 mL). The DCM phase was then dried over anhydrous $MgSO_4$, filtered and concentrated by rotary evaporation. The polymer was recovered by precipitation into large excess of diethyl ether (500 mL), isolated by filtration, and then dried under vacuum for 24 h at room temperature to get a yellow powder product (yield 45%). The conversion was 96% as determined from $^1$H NMR spectroscopy.

Table 1 summarizes the data of the functional poly (NIPAM) macro-CTAs.

TABLE 1

| Macro-CTA | Functional group | $M_n$ (SEC) | PDI | $M_n$ (NMR) | Repeating NIPAM units |
|---|---|---|---|---|---|
| 1 | Methyl- | 4300 | 1.09 | 5340 | 45 |
| 2 | Pyridine disulfide- (PDS-) | 4300 | 1.09 | 5510 | 45 |
| 3 | Dopamine- (Dopa-) | 5900 | 1.12 | 7860 | 55 |
| 4 | Biotin- | 4200 | 1.08 | 5490 | 44 |

RAFT-mediated Emulsion Polymerization of Styrene with Functional Poly(NIPAM) Macro-CTAs in Water The polymerizations were as follows: The cumulative total mass of the poly(NIPAM) macro-CTAs was (0.35 g). The other components present in the reaction mixture were styrene (0.35 g); SDS (14.5 mg), AIBN (1.2 mg), Milli-Q water (6.25 g). Dopa-poly(NIPAM) macro-CTA 3 (0.105 g, 1.33×10-5 mol), Biotin-poly(NIPAM) macro-CTA 4 (0.07 g, 1.66×10-5 mol) and SDS (7.25 mg, 5×10-5 mol) were dissolved in cold water (3.125 g) in a Schlenk tube. The mixture was deoxygenated by purging with Argon for 15 mins. AIBN (0.6 mg, 3.7×10-6 mol) was dissolved in styrene (0.175 g, 1.7×10-3) and then the solution was injected into the Schlenk flask. The mixture was then purged with Argon for another 10 mins in an ice bath before heating up to 70° C. for 3.5 h. The reaction was stopped by exposed the air at 70° C. The polymer emulsion was then characterized by SEC, $^1$H NMR and DLS. Data are shown in Table 2.

Furthermore, transmission electron microscope images of the 60% Dopa-functional/40% Biotin-functional compositions illustrate that the three dimensional structure of the composition is nanoworm. $^1$H NMR indicated an average of 45 repeating NIPAM units and 29 to 30 repeating PSTY units in each of the diblock polymers.

Coating of Nanoworms to the Surface

Glass slips (and silicon wafer) were washed successively with 10% HCl aq, acetone and methanol. The slips were then dry under nitrogen flow. To four 50 ml plastic vials (a, b, c and d), 10 mg of 60% Dopa- and 40% Biotin functional nanoworms were added in each vial and dispersed in 4 ml tris(hydroxymethyl)aminomethane (Tris) solution (10 mM, pH=8.5) and rehydrated for 20 min. Glass slips and silicon wafer were added. Then different amounts (1, 60, 120, 240 µL) of dopamine solution (33 mg/ml) were added to a, b, c and d vials, respectively. The mixture was then shaken for 4 hours. The silicon wafer was taken out and washed with water and dried for SEM images. The glass slips were washed with water and then immersed in 0.5 ml of SAv-DyLight 550 protein solution for 1 min. The slips were then washed with water again and kept in water for fluorescence microscopy.

Fluorescence images (a-d) of 60% Dopa- and 40% Biotin functional nanoworms on the glass slips with different amount of free dopamine addition ((a) 0 mg/ml, (b) 0.5 mg/ml, (a) 1.0 mg/ml and (e) 2.0 mg/ml) and then treated with SAv-550 solution showed that the incorporation of the biotin was near quantitative on the surface of the worms.

SEM of silicon wafer (e-h) coated with of 60% Dopa- and 40% Biotin functional nanoworms showed that 4 hours of coating and 1.0 mg/ml of free dopamine gave the best coating to both glass slips and silicon wafer.

Synthesis of Maleimide Functional Cationic Polymer

Synthesis of Furan-protected Maleimide Initiator

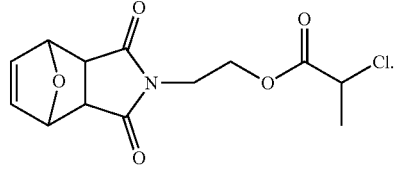 [SMILES: CC(Cl)C(=O)OCCN1C(=O)C2C3C=CC(O3)C2C1=O]

The initiator was synthesized according the literature (Geng, et al., J. Am. Chem. Soc., 2007, 129 (49), pp 15156-15163).

Synthesis of furan-protected maleimide poly-dimethylaminoEA (poly-DMAEA)

DMAEA 15 ml (0.1 mol), initiator 0.197 g (6.6×10-4 mol), $CuCl_2$ 8.8 mg (6.6×10-5 mol), Tris[2-(dimethylamino) ethyl]amine (Me6TREN) 61 mg (2.6×10-4 mol) were added in 7.5 ml of isopropanol and purged with Argon for 30 min. Cu(0) (<425 µm) 12.6 mg was added under Argon. The polymerization was allowed at room temperature for 6.5 hours with 41% conversion. The polymerization mixture was then diluted with acetone, passed through neutral $Al_2O_3$ to remove copper, the solution was concentrated and precipitated in petroleum spirit for three times and dried under high vacuum to yield 3.5 g polymer. $M_n$=9740 from NMR. FIG. 1 is a $^1$H nuclear magnetic spectrum of the polymer in deuterated chloroform ($CDCl_3$). For the polymer shown in FIG. 1, n is the integer 61.

TABLE 2

| RXN | Macro-CTA | | Conv. % | Mn(SEC) | PDI | Mn(NMR) | Mn(Theo) | Dh (nm) | PSD |
|---|---|---|---|---|---|---|---|---|---|
| 1 | 0.4 (Biotin) | 0.6 (Dopa) | 67 | 7100 | 1.18 | 8200 | 8410 | 144 | 0.24 |
| 2 | 0.4 (PDS) | 0.6 (Dopa) | 58 | 6030 | 1.23 | 8100 | 8000 | 161 | 0.03 |

Synthesis of Quaternanized Furan-protected Maleimide PDMAEA

As shown in Scheme 6, poly-DMAEA was quaternized with methyl iodide and 1-iodo-alkane with different chain lengths (as shown in Table 3). Poly-DMAEA was reacted with long chain iodo-alkane at 60° C. for 8 h. The solution was cooled to room temperature and the corresponding amount of iodomethane was added. The reaction was allowed to stir overnight at room temperature. The reaction mixture was then precipitated in acetone to give a pale yellow powder that was then dried under high vacuum.

Scheme 6

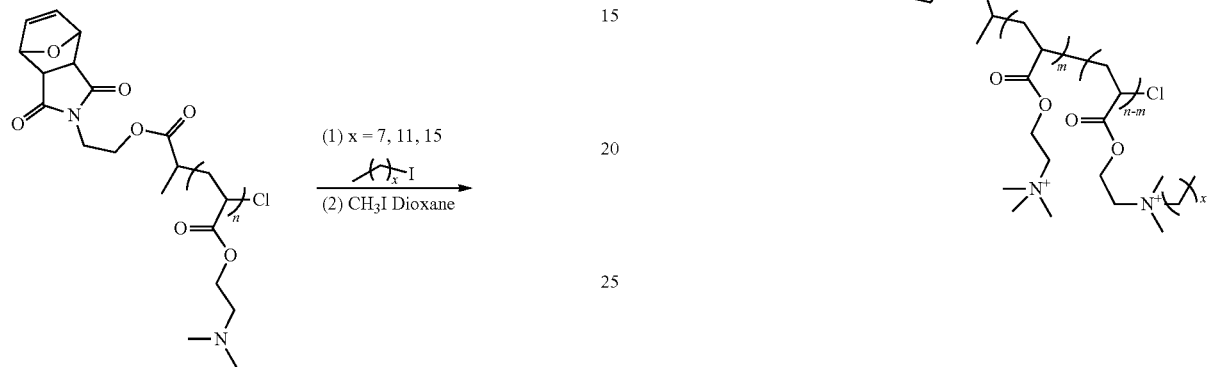

TABLE 3

|  | Ratio | MW | mol | Mass in grams | Density (g/ml$^3$) | Volume (mL) |
| --- | --- | --- | --- | --- | --- | --- |
| Polymer A |  |  |  |  |  |  |
| Poly-DMAEA | 1 | 143 | 0.002797 | 0.4 |  |  |
| 1-iodooctane | 0.1 | 240.13 | 0.00028 | 0.067169 | 1.33 | 0.0505 |
| Iodomethane | 0.9 | 142 | 0.002517 | 0.357483 | 2.28 | 0.1568 |
| dioxane |  |  |  |  |  | 3 |
| Polymer B |  |  |  |  |  |  |
| Poly-DMAEA | 1 | 143 | 0.002797 | 0.4 |  |  |
| 1-iododoecane | 0.1 | 296.23 | 0.00028 | 0.082862 | 1.2 | 0.0691 |
| Iodomethane | 0.9 | 142 | 0.002517 | 0.357483 | 2.28 | 0.1568 |
| dioxane |  |  |  |  |  | 3 |
| Polymer C |  |  |  |  |  |  |
| Poly-DMAEA | 1 | 143 | 0.002797 | 0.4 |  |  |
| 1-iodohexadecane | 0.1 | 352.34 | 0.00028 | 0.098557 | 1.121 | 0.0879 |
| Iodomethane | 0.9 | 142 | 0.002517 | 0.357483 | 2.28 | 0.1568 |
| dioxane |  |  |  |  |  | 3 |

Deprotection of Quaternanized Furan-protected Maleimide Poly-DMAEA

As shown in Scheme 7, quaternized poly-DMAEA was then dissolved in DMSO (0.2 g, in 4 ml) and then heated at 120° C. for 3 hours. The residual was then precipitated in acetone to yield pale brown polymer material. The polymer was characterized by NMR to confirm the maleimide chain end. The percentage of long carbon chains was very close to the target amount (~10%).

Scheme 7

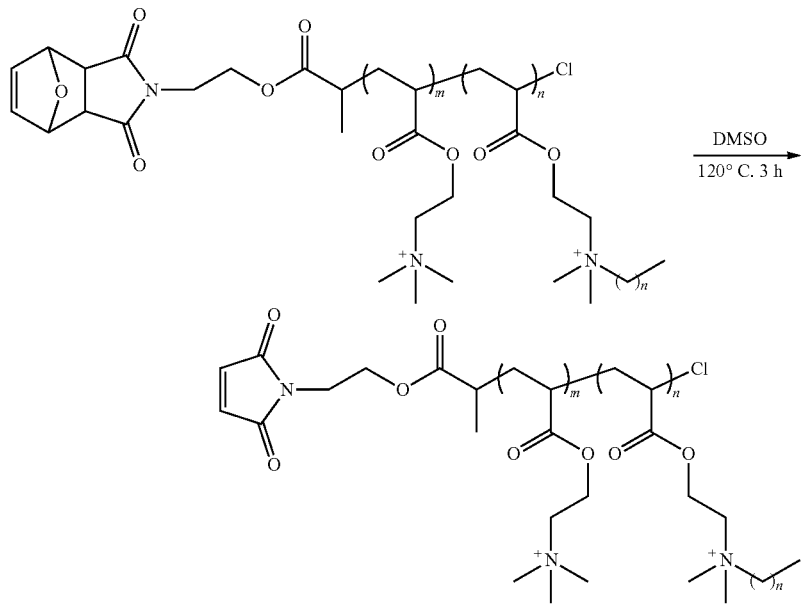

Figure 2A:
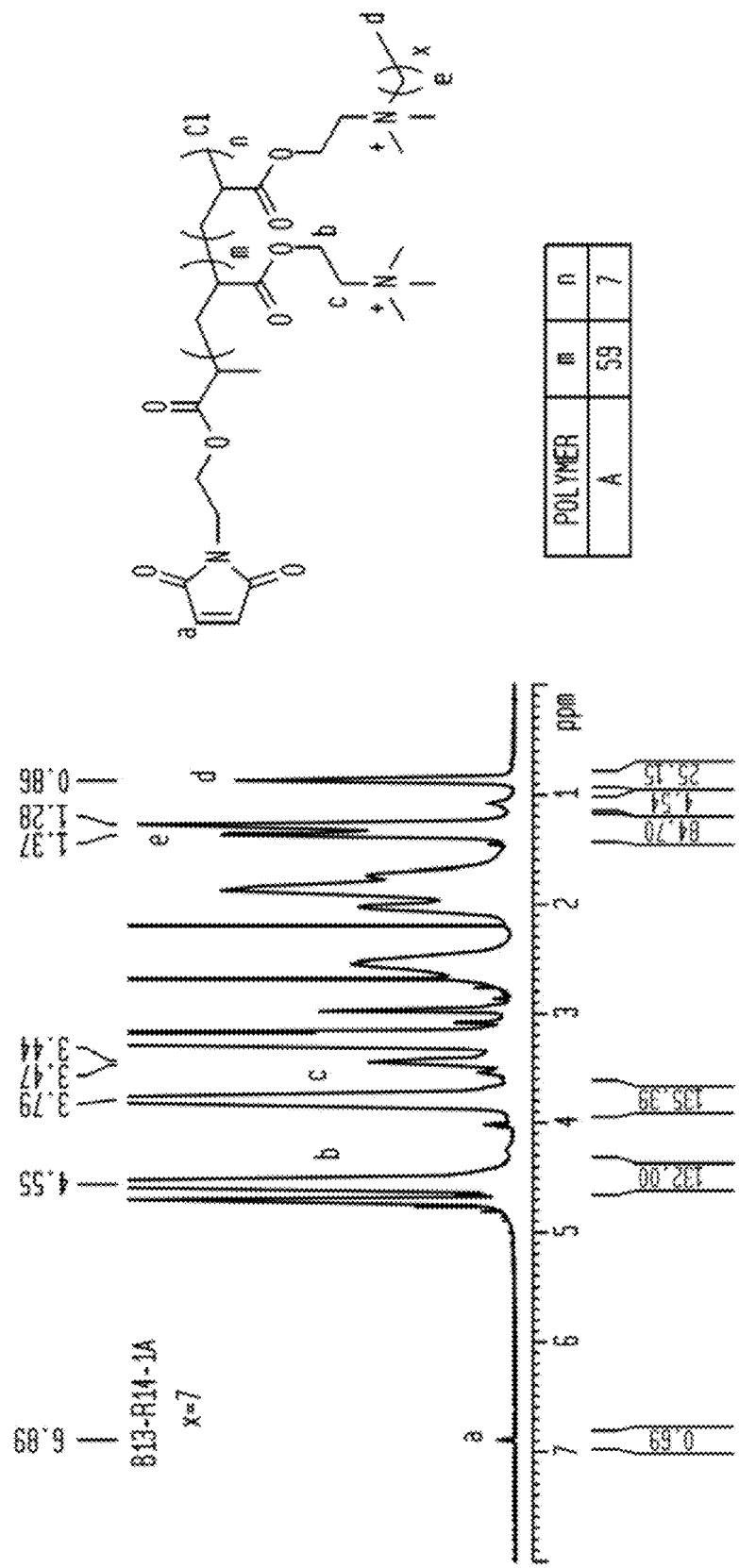
FIG. 2A is a $^1$H NMR spectrum of maleimide functional quaternized-poly-DMAEA in deuterated water, according to one aspect.

FIGS. 2A, 2B, and 2C illustrate $^1$H NMR spectra of maleimide functional quaternized-poly-DMAEA in $D_2O$. (n=61) (FIG. 2A) 10 mol % 1-iodooctane, (FIG. 2B) 10 mol % 1-iodododecane and (FIG. 2C) 10 mol % 1-iodohexadecane. Conjugation of Maleimide Functional Cationic Polymers to the Dopa- and PDS-functional Nanoworms FIG. 3 is a scheme illustrating conjugation of maleimide functional cationic polymer to Dopa- and PDS- functional nanoworms. Maleimide functional cationic polymer A, B, or C (12.7 mg each) was added to an Eppendorf tube and 1 ml of water was added. After the polymer dissolved, a solution of polymer A, B, or C was added to another Eppendorf tube comprising the nanoworms Dopa-(60%) and PDS- (40%) (20 mg of nanoworm). Then 10 µl TCEP solution (32.5 mg/ml) was added, the Eppendorf tube was wrapped with aluminum foil (protection from light), and the tube was shaken overnight. The final product had the chemical structure shown below, where Nanoworm A had n=7, Nanoworm B had n=11, and Nanoworm C had n=15.

Antibacterial Testing

Antibacterial Testing for Maleimide Functional Cationic Polymer A, B and C in Solution Experimental set-up For Maleimide functional cationic polymer A, B and C a solution of 5 mg/ml was made in water.

In a 24 well plate 500 µl of polymer solutions in water were added in duplicates and 500 µl of water added to wells that contain LB blank and E.coli.

500 µl of E. coli solution 1×10$^5$ cells/ml was added to the wells containing polymer in water. 500 µl LB added to blank wells.

Top of the plate was covered with parafilm before the lid was placed on and then more parafilm was used to seal the edges to stop solvent evaporation.

Plate was then placed in 37° C. incubator with shaking at 120 rpm for 14 hours.

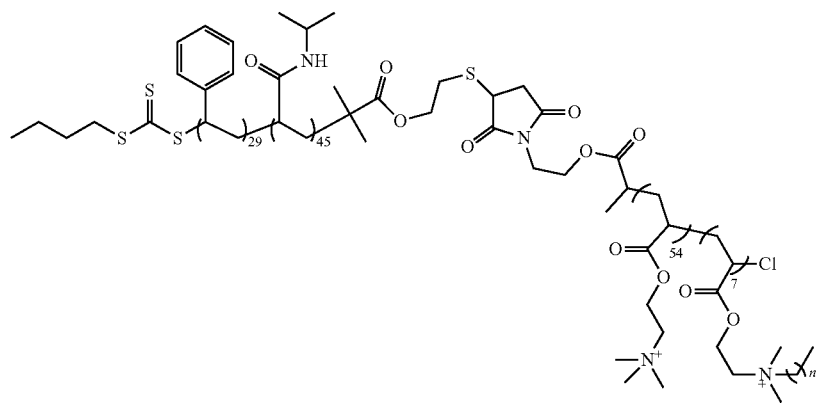

n = 7, 11, 15

Figure 4:
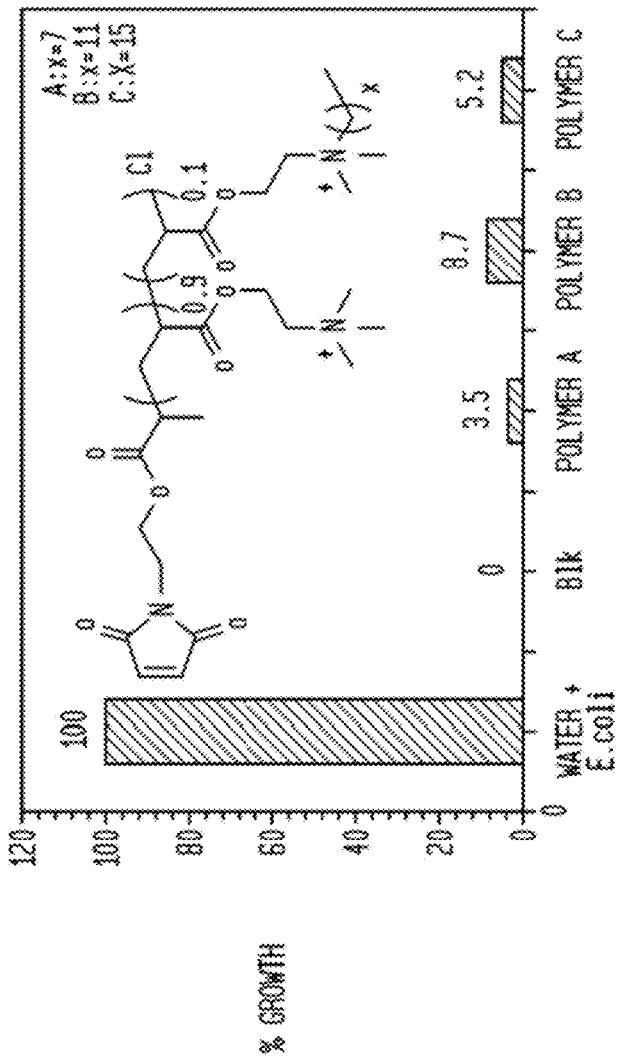
FIG. 4 is a bar graph illustrating the inhibitory effects of several polymers of the present disclosure against *E. coli* cultures, according to one aspect.

The antibacterial activity of the polymers were measured based on the optical density of the *E.coli* cultures. FIG. 4 is a bar graph illustrating the inhibitory effects of the polymers against *E. coli* cultures. All three polymers showed great inhibition of bacterial growth (>90%).

Antibacterial Testing for Functional Cationic Nanoworms A, B and C in Solution.

Experiment Set-up

For nanoworms A, B, and C, a solution of 5 mg/ml was made in water.

In a 24 well plate 500 µl of nanoworm solutions in water were added in duplicates and 500 µl of water added to wells that will contain LB blank and *E.coli*.

500 µl of *E.coli* solution 1×10$^5$ cells/ml was added to the wells containing polymer in water. 500 µl LB added to blank wells.

Top of the plate was covered with parafilm before lid was placed on and then more parafilm was used to seal the edges to stop evaporation.

Plate was placed in 37° C. incubator with shaking at 120 rpm for 14 hours.

Could not measure *E.coli* by the usual method of measuring OD due to the color of the solution.

*E.coli* growth was monitored by plating out nanoworm/ *E.coli* solutions on LB agar plates. Dilutions were done in LB and 20 µl plated and left in the incubator O/N.

Figure 5A:
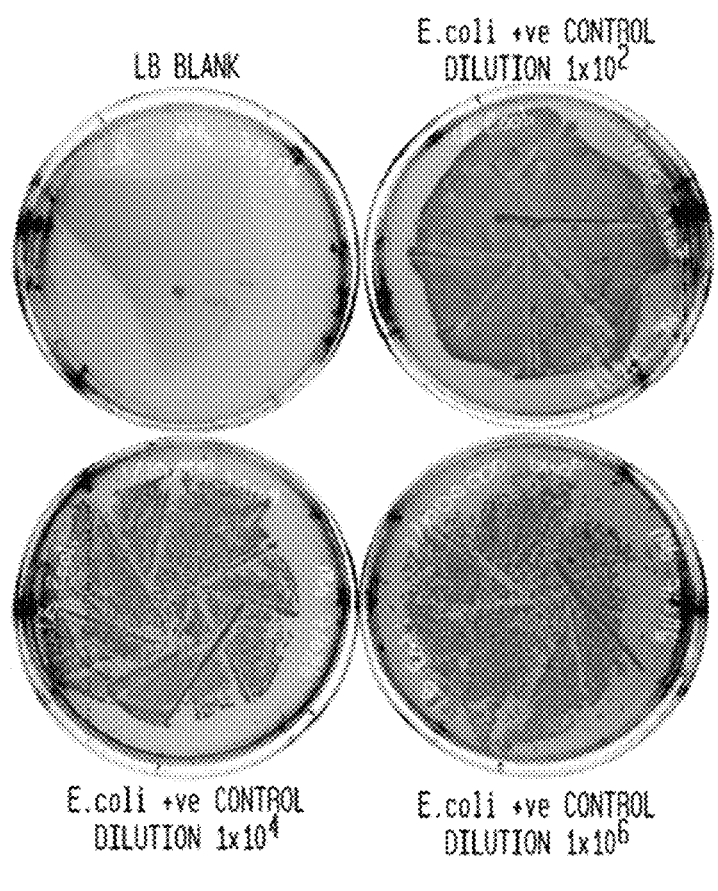
FIG. 5A is scanning electron microscope images showing a blank and *E.Coli* control, according to one aspect.
Figure 5B:
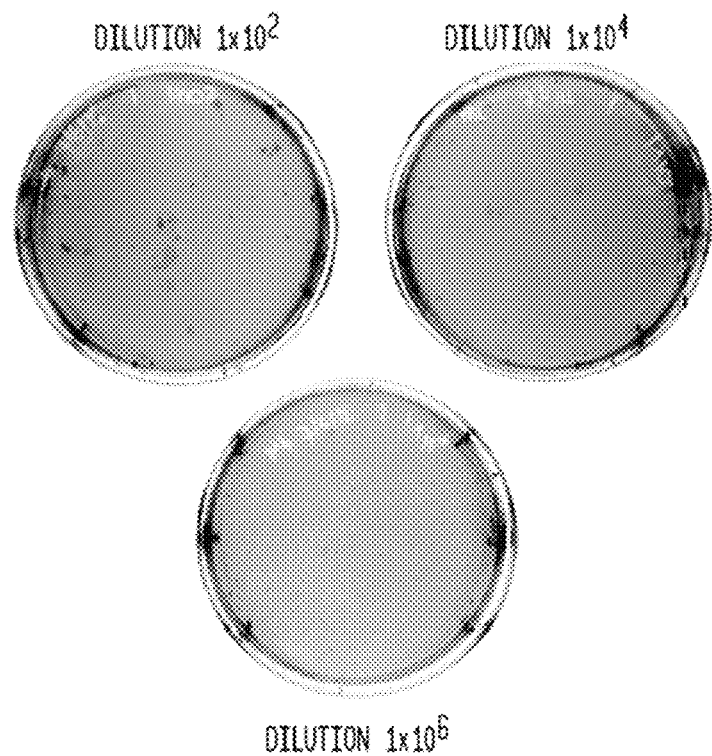
FIG. 5B is scanning electron microscope images showing antibacterial activity of several cationic polymer nanoworms of the present disclosure against *E.coli*, according to one aspect.
Figure 5C:
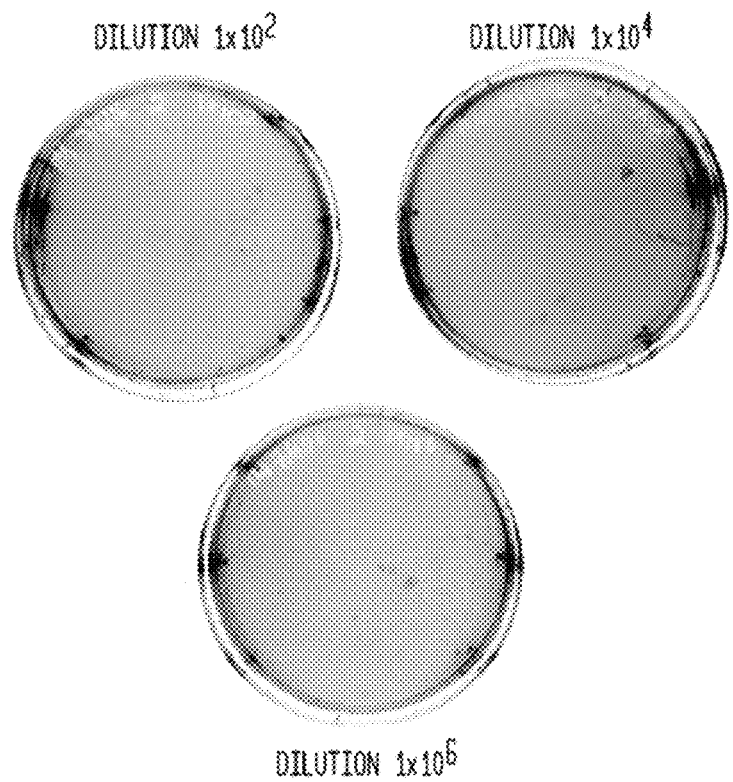
FIG. 5C is scanning electron microscope images showing antibacterial activity of several cationic polymer nanoworms of the present disclosure against *E.coli*, according to one aspect.
Figure 5D:
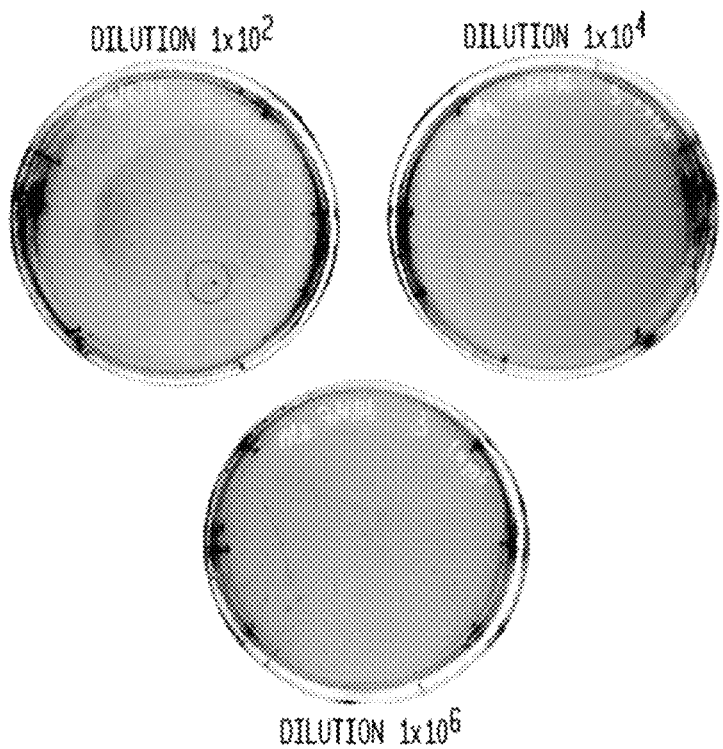
FIG. 5D is scanning electron microscope images showing antibacterial activity of several cationic polymer nanoworms of the present disclosure against *E.coli*, according to one aspect.

FIGS. 5A-5D are scanning electron microscope images showing the antibacterial activity of the cationic polymer nanoworms A, B, and C against *E.coli*. (FIG. 5A) LB Blank and *E.Coli* control, (FIG. 5B) nanoworms B, (FIG. 5C) nanoworms C and (FIG. 5D) nanoworms D all with different dilution (102, 104, and 106) as indicated in the figure. All nanoworms were able to kill the bacteria to almost 100%. Only one *E.coli* colony seen (circled in FIG. 5D). On the contrast, there are many *E.coli* colonies seen on the +ve control plates (FIG. 5A). This indicated the cationic polymer nanoworms can efficiently kill almost all the *E.coli*.

Overall, it has been shown that by using SAv-Biotin binding experiment and SEM, it has been demonstrated that the nanoworms can be effectively coated on the glass slips and silicon wafer. The maleimide functional cationic polymers showed great inhibition of E.coli growth (>90%). Further conjugation of these maleimide functional nanoworms onto the PDS- and Dopa functional nanoworms retain the antibacterial properties.

Overall, compounds and compositions of the present disclosure can provide an antimicrobial nanostructure capable of targeted binding to microbes and cell degeneration of the microbes. The ratiometric control of functionality of compositions of the present disclosure provides an ability to target and degenerate a wide range of microbes from bacteria to viruses.

DEFINITIONS

The term "pharmaceutically-acceptable" means suitable for use in pharmaceutical preparations, generally considered as safe for such use, officially approved by a regulatory agency of a national or state government for such use, or being listed in the U.S. Pharmacopoeia or other generally recognized pharmacopoeia for use in animals, and more particularly in humans.

The term "pharmaceutically-acceptable salt" refers to a salt which may enhance desired pharmacological activity. Examples of pharmaceutically-acceptable salts include acid addition salts formed with inorganic or organic acids, metal salts and amine salts. Examples of acid addition salts formed with inorganic acids include salts with hydrochloric acid, hydrobromic acid, sulfuric acid, nitric acid and phosphoric acid. Examples of acid addition salts formed with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxy-benzoyl)-benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methyl-bicyclo[2.2.2]oct-2-enel-carboxylic acid, gluco-heptonic acid, 4,4'-methylenebis(3-hydroxy-2-naphthoic) acid, 3-phenylpropionic acid, trimethyl-acetic acid, tertiary butylacetic acid, lauryl sulfuric acid, gluconic acid, glutamic acid, hydroxy-naphthoic acids, salicylic acid, stearic acid and muconic acid. Examples of metal salts include salts with sodium, potassium, calcium, magnesium, aluminum, iron, and zinc ions. Examples of amine salts include salts with ammonia and organic nitrogenous bases strong enough to form salts with carboxylic acids.

The term "therapeutically-effective amount" refers to an amount of a compound that, when administered to a subject for treating a condition, is sufficient to effect treatment for the condition. "Therapeutically effective amount" can vary depending on the compound, the condition and its severity, the age, and the weight of the subject to be treated.

The term "virus" refers to a submicroscopic infective agent that includes a nonliving complex molecule that typically contains a protein coat surrounding an RNA or DNA core of genetic material but no semipermeable membrane, that is capable of growth and multiplication in living cells, and that can cause a disease in humans, animals, or plants.

Compounds of the present disclosure include tautomeric, geometric or stereoisomeric forms of the compounds. Ester, oxime, onium, hydrate, solvate and N-oxide forms of a compound are also embraced by the present disclosure. The present disclosure considers all such compounds, including cis- and trans-geometric isomers (Z- and E-geometric isomers), R- and S-enantiomers, diastereomers, d-isomers, l-isomers, atropisomers, epimers, conformers, rotamers, mixtures of isomers and racemates thereof are embraced by the present disclosure.

The descriptions of the various aspects of the present disclosure have been presented for purposes of illustration, but are not intended to be exhaustive or limited to the aspects disclosed. Many modifications and variations will be apparent to those of ordinary skill in the art without departing from the scope and spirit of the described aspects. The terminology used herein was chosen to best explain the principles of the aspects, the practical application or technical improvement over technologies found in the market-

What is claimed is:

1. A compound of formula (I):

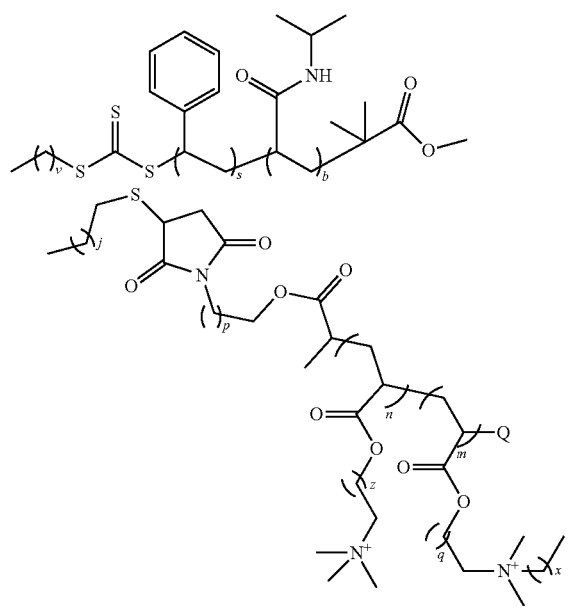

(I)

or a pharmaceutically acceptable salt thereof, wherein:
Q is fluoro, chloro, bromo, or iodo;
s is an integer from 10 to 100;
b is an integer from 10 to 100;
n is an integer from 10 to 100;
v is an integer from 1 to 20;
j is an integer from 1 to 20;
p is an integer from 1 to 20;
z is an integer from 1 to 20;
q is an integer from 1 to 20;
x is an integer from 1 to 20; and
m is an integer from 1 to 20.

2. The compound of claim 1, wherein s is an integer from 25 to about 35.

3. The compound of claim 2, wherein b is an integer from 40 to 50.

4. The compound of claim 3, wherein n is an integer from 50 to 60.

5. The compound of claim 4, wherein m is an integer from 5 to 10.

6. The compound of claim 5, wherein Q is chloro.

7. The compound of claim 1, wherein x is an integer from 5 to 15.

8. The compound of claim 1, wherein the ratio of the integer n to the integer m is from 5:1 to about 15:1.

9. The compound of claim 1, wherein the compound is of formula (II):

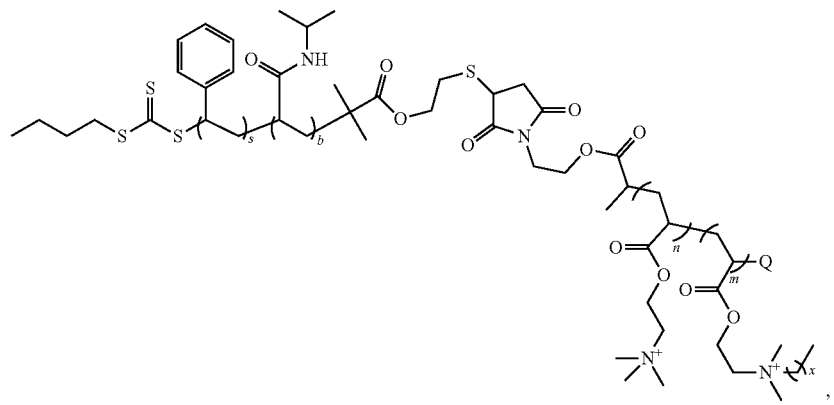

(II)

or a pharmaceutically acceptable salt thereof, wherein:
Q is fluoro, chloro, bromo, or iodo;
s is an integer from 10 to 100;
b is an integer from 10 to 100;
n is an integer from 10 to 100;
x is an integer from 1 to 20; and
m is an integer from 1 to 20.

10. The compound of claim 9, wherein s of formula (II) is an integer from 25 to 35.

11. The compound of claim 10, wherein b of formula (II) is an integer from 40 to about 50.

12. The compound of claim 11, wherein n of formula (II) is an integer from 50 to 60.

13. The compound of claim 12, wherein:
m of formula (II) is an integer from 5 to 10, and
x of formula (II) is an integer from 5 to 15.

14. The compound of claim 9, wherein the compound is of formula (III):

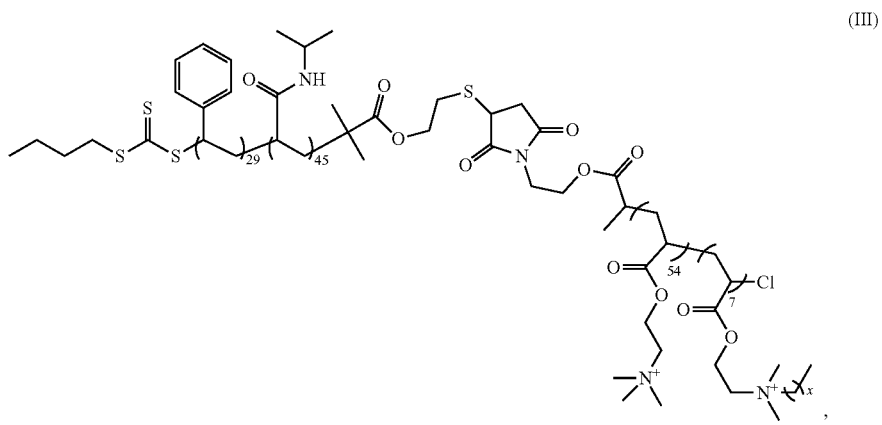

(III)

or a pharmaceutically acceptable salt thereof, wherein x is an integer from 5 to 15.

15. A composition comprising:
the compound of claim 1; and
a compound of formula (IV):

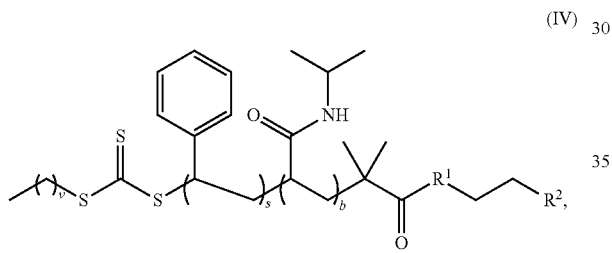

(IV)

or a pharmaceutically acceptable salt thereof, wherein:
each of s and b of formula (IV) is independently an integer from 10 to about 100;
v of formula (IV) is an integer from 1 to 20;
$R^1$ is —O— or —NH—; and
$R^2$ is —CH$_3$, biotin, pyridyl disulfide,

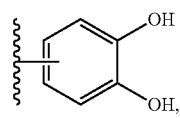

thiolactonyl, or adamantyl.

16. The composition of claim 15, wherein:
s of formula (IV) is an integer from 25 to 35,
b of formula (IV) is an integer from 40 to 50, and
v of formula (IV) is 2.

17. The composition of claim 15, wherein $R^2$ is

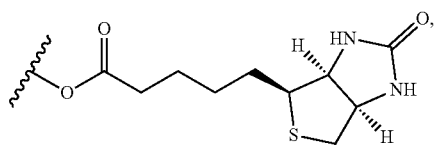

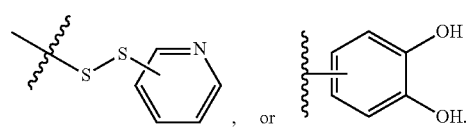

18. The composition of claim 15, wherein the compound of formula (IV) is one or more of:

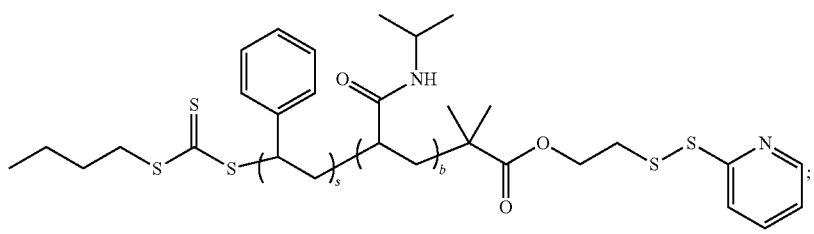

-continued

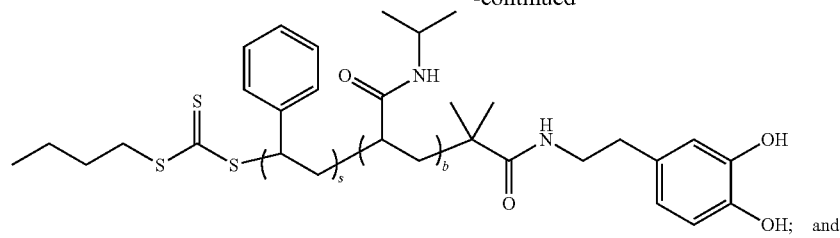

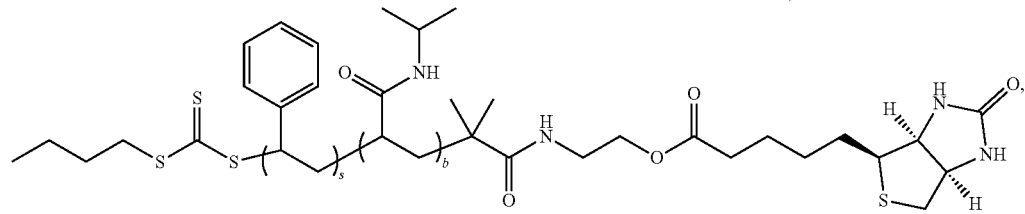

wherein s of formula (IV) is an integer from 25 to about 35 and b of formula (IV) is an integer from 40 to 50.

19. The composition of claim 15, wherein the composition has a 3-dimensional structure that is a nanoworm or nanorod.

20. The composition of claim 19, wherein the composition is a nanorod having a diameter from about 10 nm to about 20 nm and a length from about 1 micron to about 2 microns.

21. The compound of claim 1, wherein the compound is a pharmaceutically acceptable salt.

22. The pharmaceutically acceptable salt of claim 21, wherein the salt is an iodo salt.

UNITED STATES PATENT AND TRADEMARK OFFICE
CERTIFICATE OF CORRECTION

PATENT NO. : 10,428,020 B2  
APPLICATION NO. : 15/838751  
DATED : October 1, 2019  
INVENTOR(S) : Michael Monteiro et al.

Page 1 of 1

It is certified that error appears in the above-identified patent and that said Letters Patent is hereby corrected as shown below:

In the Claims

In Column 42, Line 15, in Claim 1, delete "1to" and insert -- 1 to --, therefor.

In Column 42, Line 17, in Claim 2, after "to" delete "about".

In Column 42, Line 30, in Claim 8, after "to" delete "about".

In Column 42, Line 62, in Claim 11, after "to" delete "about".

In Column 43, Line 42, in Claim 15, after "to" delete "about".

In Column 45, Line 21, in Claim 18, after "to" delete "about".

Signed and Sealed this  
Ninth Day of June, 2020

Andrei Iancu  
*Director of the United States Patent and Trademark Office*